United States Patent
Markovic et al.

[11] Patent Number: 6,143,512
[45] Date of Patent: Nov. 7, 2000

[54] CAP-PAP TEST

[76] Inventors: Nenad Markovic; Olivera Markovic, both of 259 Congressional La., #602, Rockville, Md. 20852

[21] Appl. No.: 09/329,445

[22] Filed: Jun. 10, 1999

Related U.S. Application Data

[60] Provisional application No. 60/096,744, Aug. 17, 1998.
[51] Int. Cl.[7] ............................. C12Q 1/42; C12Q 1/00; G01N 33/53
[52] U.S. Cl. .................. 435/21; 435/4; 435/7.9; 435/7.1; 435/283.1; 435/975
[58] Field of Search ................. 435/21, 4, 7.9, 435/7.1, 283.1, 975

[56] References Cited

U.S. PATENT DOCUMENTS

| | | | |
|---|---|---|---|
| 3,991,705 | 11/1976 | Adler | 435/21 |
| 4,059,404 | 11/1977 | Schuster et al. | 435/21 |
| 4,120,262 | 10/1978 | Adler et al. | 435/21 |
| 4,175,860 | 11/1979 | Bacus | 435/21 |

(List continued on next page.)

OTHER PUBLICATIONS

J. Histotech, vol. 22(1), pp. 43–48, Mar. 1999.
Invention Disclosure. CAP–PAP Test for Cervical cancer Screening. USPTO #426,850, Oct. 24, 1997.
Provisional Patent Application. CAP–PAP (Cervical Acid Phosphatase—Papanicolaou) Test, Processes of Producing and Manner of Using the Same. USPTO #60/096744, Aug. 17, 1998.

(List continued on next page.)

*Primary Examiner*—Louise N. Leary

[57] ABSTRACT

The CAP-PAP Test is a double-staining, single-slide microscopic method. An in vitro diagnostic medical device for manual and automatic staining and interpreting of the Pap smear for cervical cancer screening, cervical dysplasia and for follow-up therapy can be developed using this double-staining, single-slide microscopic method. Abnormal cervical cells are labeled with an intracellular acid phosphatase derived pigment (azo-dye) to improve visibility of abnormal cervical cells on conventionally stained Pap smears. The enzyme marker improves human perception and/or sensitivity of automatic instruments when distinguishing cell a abnormality and interpretation of Pap smears. Increased accuracy of CAP-PAP-vs-Pap test is expected to reduce false negative readings of the conventional Pap test. A rapid manual version of the test that is low cost, does not require additional personnel training and is instantly applicable in all cytopathology laboratories is provided. The invention further provides a diagnostic kit, an automatic stainer and an automatic evaluation device for performing the double-staining, single-slide microscopic method.

3 Claims, 3 Drawing Sheets

(3 of 3 Drawing Sheet(s) Filed in Color)

COLOR PLATE 1

U.S. PATENT DOCUMENTS

| | | | |
|---|---|---|---|
| 4,206,280 | 6/1980 | Gallati et al. | 435/21 |
| 4,362,386 | 12/1982 | Matsushita et al. | 435/21 |
| 4,384,587 | 5/1983 | Milgrom | 435/21 |
| 4,523,278 | 6/1985 | Reinhardt et al. | 435/21 |
| 4,550,016 | 10/1985 | Harris | 435/21 |
| 4,633,886 | 1/1987 | Bucaro | 435/21 |
| 4,714,606 | 12/1987 | Kass | 435/21 |
| 4,853,210 | 8/1989 | Kass | 435/21 |
| 4,862,899 | 9/1989 | Bucaro | 435/21 |
| 4,983,512 | 1/1991 | Teshima et al. | 435/21 |
| 5,081,274 | 1/1992 | Kuroiwa et al. | 435/21 |
| 5,121,752 | 6/1992 | Canna et al. | 435/21 |
| 5,227,291 | 7/1993 | Kuroiwa et al. | 435/21 |
| 5,257,182 | 10/1993 | Luck et al. | 435/21 |
| 5,328,826 | 7/1994 | Nozana et al. | 435/21 |
| 5,352,613 | 10/1994 | Tafas et al. | 435/21 |
| 5,422,277 | 6/1995 | Connelly et al. | 435/21 |
| 5,496,704 | 3/1996 | Fiedler et al. | 435/21 |
| 5,635,402 | 6/1997 | Alfano et al. | 435/21 |
| 5,695,942 | 12/1997 | Farmilo et al. | 435/21 |
| 5,698,162 | 12/1997 | Belly et al. | 435/21 |
| 5,713,369 | 2/1998 | Tao et al. | 435/21 |
| 5,719,030 | 2/1998 | Kuroiwa et al. | 435/21 |

OTHER PUBLICATIONS

NIH Consensus Conference on Cervical Cancer, 1996. NIH, Bethesda, MD. (Http://text.nlm.nih.gov), and Cervical Cancer. NIH Consens Statement 1996 Apr. 1–3; 14(1):1–38.

ACS Screening Recommendations for the Early Detection of Cancer. Web Page: www.texmed.org/health_science/poep/hs_poepcancer.html (Apr. 1, 1999).

Papanicolaou GN. A New procedure for staining vaginal smears. *Science* 1948, 95(2469):438–39.

Who Releases. Report on Cervical Cancer Screening (www-.paptest.com/dwnlds/who.txt).

Neopath: Clinical Update in Modern Cytology. Automation in Primary Screening. AutoPap. 1998 Neopath. Inc., and Marshall J. AutoPap Experience: False Negative/False positive Problems—Laboratory issues—Clinician Issues—Current Practice vs. AutoPap. Invited lecture. Conference on Automated Solutions in Cervical Cancer Prevention. McLean, VA, Jul. 29, 1998; and NeoPath Inc.: www.neopath.com/product (Apr. 1, 1999.

Ritchie AC. Boyd's Textbook of Pathology, Female Reproductive System, Tumors. Ninth Edition. Lea & Febiger, Philadelphia, 1990; pp. 1365–72.

Koss LG. The Papanicolaou Stain. In Koss LG. *Diagnostic Cytology and its Histopathology Basis.* 4$^{th}$ Ed. Lippincott, Philadelphia, 1992. pp. 1474–1492.

Mac Kay T.H. Cervical intraepithelial neoplasia (CIN: Dysplasia if the cervix). In L.M. Tierney, S.J. McPhee, M.A. Papadakis (Eds) 1997 *Current Medical Diagnosis and Treatment,* 36 ed. Appleton & Lange publishers, 1997; pp. 674–675.

Cytus Inc.: The ThinPrep System—How it works. Web Page: www.cytus.com/85506Prd/prepwork.htm. (Apr. 1, 1999).

NetMed: Papnet—How Papnet works. Web Page: www.papnet-ohio.com/more.htm (Apr. 1, 1999).

CompuCyte, Inc.: The LSC Laser Scanning Cytometer. Web Page: www.CompuCyte.com/prodinfo.html (Apr. 1, 1999).

AccuMed Int.: AcCell Cytopathology System. Web Page:www.accumed.com/cyto/accell/html (Apr. 1, 1999).

AutoCyte Inc. AutoCyte Prep and AutoCyte Screen for Cervical cancer Screening. Web Page: www.prnewswire-.com/cgi–bin/story (story 02–09–1999)(Apr. 1, 1999).

Digene: Hybrid Capture Technology. Web Page: www.digene.com/customer/techsup/hcs_tech.htm (Apr. 1, 1999).

Diadexus: Diadexsus and Cancer Research Campain Technology. Web Page: diadexus.com/news/releases/980922.html (Apr. 1, 1999).

Pizzi A, Metz JL. Diagnostic Cytology Learning Page. Web Site: www–osc.colorado.edu/~metzj/pizzia/learning_page.html (Apr. 1, 1999).

BSC–98–02: Study of the CAP–PAP Test Safety and Efficacy for Cervical Cancer Screening in Comparison with the Standard Pap Test. SBIR Phase 1 Grant Application. Dec. 15, 1998 Deadline. See Ref.#49.

BSC–98–03: A Phase II Clinical Trial to Compare Safety and Accuracey of the CAP–PAP and the Conventional Pap Test to Detect Precancerosis, and to Prevent Cervical cancer in Women with "Nonnegative" Primary pap Smear. SBIR Phase 2 Grant Proposal. Dec. 15, 1998, Deadline.

NCCC: Worldwide Cervical Cancer Issues. Web Page: www.nccc–online.org/worldcancer.html (Apr. 1, 1999).

Goldberg AF, Barka T: Acid phosphatase activity in human blood cells. *Nature* 195: 197, 1962.

Akimoto S, Mosai M, Akamura K: Tumor marker doubling time in patients with prostate cancer:determination of prostate specific antigen and prostatic acid phosphatase. *Europ Urol* 27:207–12, 1995.

Markovic O, Shulman NR: Megakaryoctye maturation indicated by methanol inhibition of an acid phosphatase shared by megakaryocytes and platelets. In *Megakaryoctye Biology and Cellular Properties.* Ewatt B, Levin R (eds), Elsevier North Holland Inc, New York, 1981, pp. 271–283.

Bunn P: Tumor markers. In *Cecil Textbook of Medicine,* Wingaarden J, Smith L, Bennett C (eds), WB Sounders Co, Philadelphia, 1992, pp. 1034–1037.

Markovic O: Cytochemistry of megakaryocytes.. *ZB Med Fak Skopje* 22: 91–117, 1976. (Three articles).

Markovic O, Markovic N: Cytochemistry and immunocytochemistry in the classification of blood marrow and blood cells and in the diagnosis of hematologic disorders. In *Electronmicroscopic Cytochemistry and Immunocytochemistry in Biomedicine.* Ogawa K, Barka T (eds). CRC Press, Boca Raton, 1993, pp. 611–638.

Yam LT, Li CL, Lam KW: Tartrate resistant isoenzyme in reticulum cells of leukemic reticuloendotheliosis. *New Engl J Med* 284:357–9, 1971.

Van Der Heuvel R, Mathieu E, Schoeters G et al: Stromal cells from murine developing hemopoietic organs: comparison of colony–forming unit of fibroblasts in long–term cultures. *Int J Dev Biol* 35:33–41, 1991.

Sidqui M, Collins P, Vitte C et al: Osteoblast adherence and resorption activity of isolated osteoclasts on calcium sulphate hemihydrate. *Biomaterials* 16:1327–9, 1991.

Markovic O: Platelet acid phosphatase isoenzymes. II Congress of Yugoslavian Hematologists. Proceedings 1:801–5, 1974; and Markovic O: Cytochemistry of megakaryocytes. 2. Acid phosphatase: separation of acid phosphatase isoenzymes. *Mak Med Pregl* 30:19–27, 1975. See Ref.#30.

Scambia G, Benedetti P, Ferradina G et al: Cathepsin D assay in ovarian cancer; correlation with pathologic features and receptors for estrogen, progesterone and epidermal growth factor. *Brit J Cancer* 64:182–4, 1991.

Sloan B, Moin K, Sameni M: Membrane association of cathepsin B can be induced by transfection of human breast epithelial cells with c–ha–ras oncogene. *J Cell Sci* 107:373, 1994.

Garcia M, Derock D, Pujon P et al: Overexpression of transfected cathepsin D in transformed cells increases their malignant phenotype and metastatic potency. *Oncogene* 5:1809–14, 1990.

Saeed S, Stock–Novak D, Pohlod R et al: Prognostic correlation of plasma cell acid phosphatase and beta–glucuronidase in multiple myeloma. *Blood* 78:3281–7, 1991.

Zhou R, Sause WT, Hammond EH et al: Correlation of survival with quantitative tissue staining of prostate specific acid phosphatase in patients with prostate cancer. *Int J Radiat Biol Phys* 33: 823–9, 1995.

Acid phosphatase in vaginal smears—semen (forensic analyses) List of literature not included for this submission.

Gross SJ, Kinzie G. Cytochemistry of benign and malignant squamous epithelium of the cervix uteri. *Obst and Gynec.* 1960;15:261–79.

Berger J. Histochemistry of ectopia, ectropion and epidermization. Symposium on premalignant cervical lesions. *Acta Cytol.* 1961; 5:61–4.

Malvi SG, Sirsat SM. A cytochemical study of acid phosphatase in carcinoma of the cervis uteri. The *Indian Journal of Cancer* 1974; 11(1):81–7.

Gomori G. The lead nitrate method for acid phosphatase. In A.G.E. Pierse. *Histrochemistry,* Theoretical and practical. 3d ed. Williams & Wilkins, 1968, pp. 554, 730.

Panazzolo A, Bergantino L, Arrotta S, Napoli F, and Pacilli L. Gli enzimi lisosomiali nella patologia neoplastica del collo dell'utero. *Min. Gin.* 1978; 30:1123–45. (Italian).

Preliminary Studies: Markovic O, Markovic N. Acid phosphatase in cervical cells (unpublished data). Not available at this moment.

Markovic O, Markovic N: May Acid phosphatase decrease Pap test false engative readings. *J Nat Cancer Inst* 89:1459, 1997.

Markovic O: Cervical acid phosphatase–Panpanicolaou test. *SBIR Project Proposal,* NIH, Bethesda, MD, 1998. See Ref.#23..

Markovic O, Markovic N. Acid Phosphatase in Cervical Smears (CAP–PAP test). *Arch Onc* 1998; 6(3):137–9.

Markovic O, Markovic N, Belledonne M. Cervical Acid Phosphatase—Papanicolaou (CAP–PAP) Test. *J. Histotechnology* 1999; 22(1):43–47.

Sigma Chem. Co. St. Louis, MO. Sigma technical procedure No. 387, 1993; and No. HT40, Papanocolaou Staning System, 1994.

Burstone MS: *Enzyme Histochemistry and Its Application in the Study of Neoplasms.* Academic Press, NY, 1962, pp. 88–113.

Baker A, Melcher DH: Rapid cervical cytology screening. *Cytopathology* 2,299–301, 1991.

Baker RW, Wadswortj, Brugal G et al: An evaluation of "rapid review" as a method of quality control of cervical smears using Axio–Home microscope. *Cytopathology* 8:85–95, 1997.

Farrell DJ, Bilkhu S, Gibson L, Cummings L et al: Rapid screening of cervical smears as a method of internal quality control. *Acta Cytol* 41:251–60, 1997.

Dudding N: Rapid screening of cervical smears: An improved method of quality control. *Cytopathology* 6:95 99, 1995.

Van Der Graff Y, Vooijs GP, Gallard HJ et al: Screening errors in cervical cytology screening. *Acta Cytol* 31:434–438, 1987.

Markovic N, Markovic O, Markovic S: Image processing assisted measurement of intracellular effects of enzyme targeted drugs. *Cell Vision* 2:71–78, 1995.

National Coalition for Cervical Cancer. What is the level of reimbursement for the Pap and why is this rate inadequate? Web Page:www.nccc–online.org/ncccfq.asp (Feb. 8, 1999).

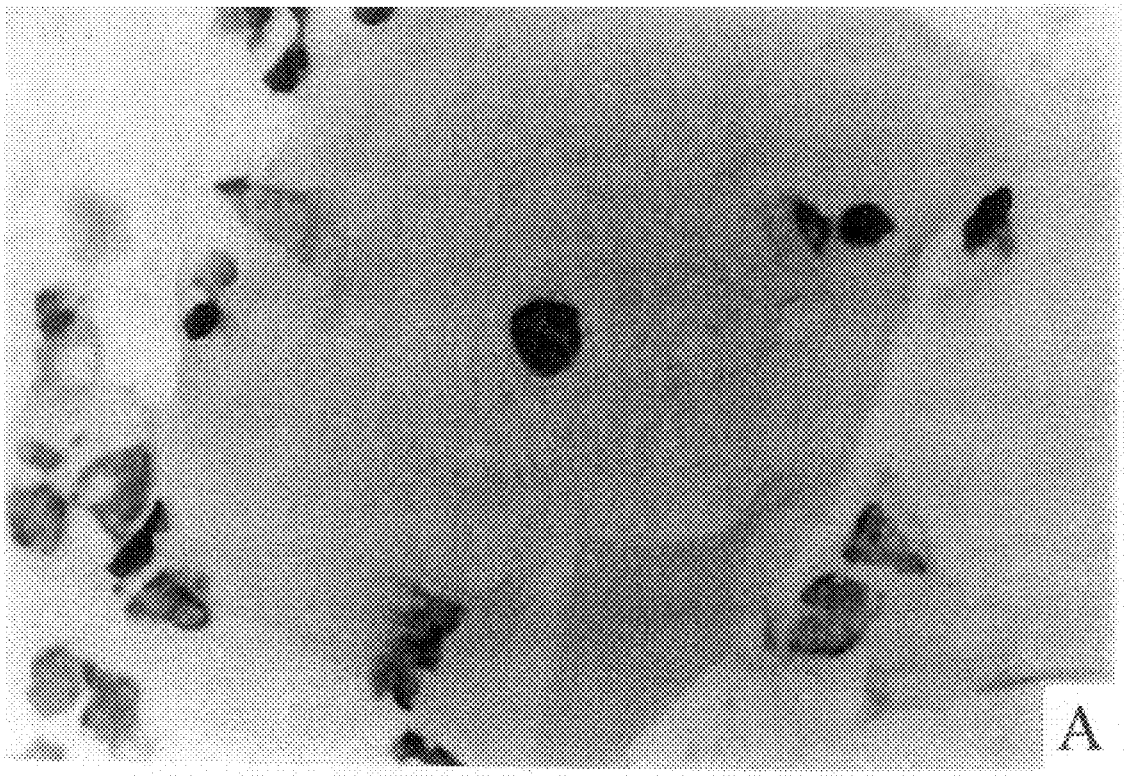
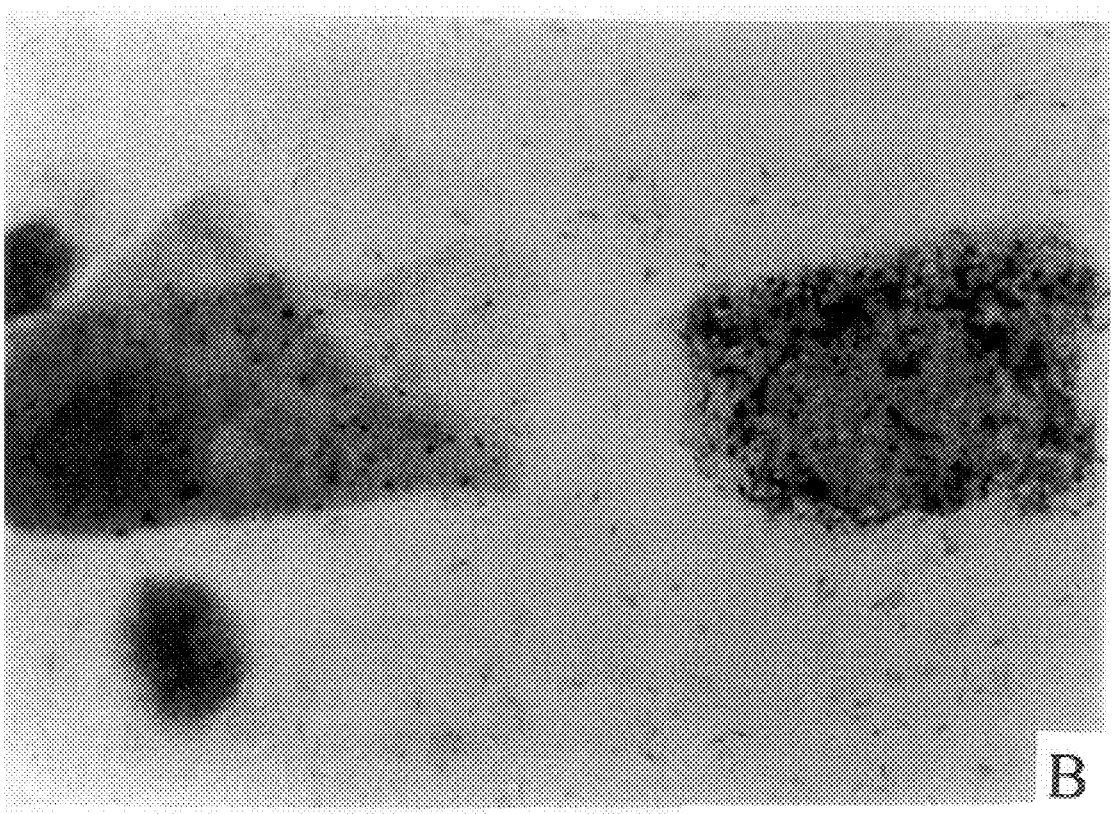
COLOR PLATE 1

COLOR PLATE 2
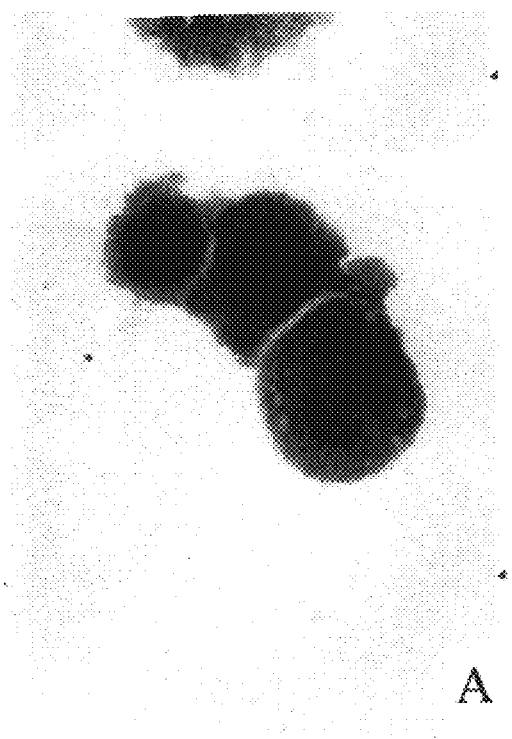
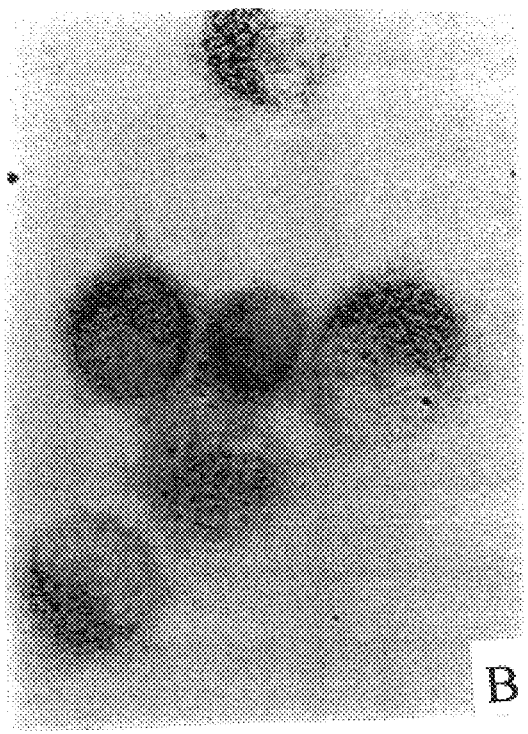
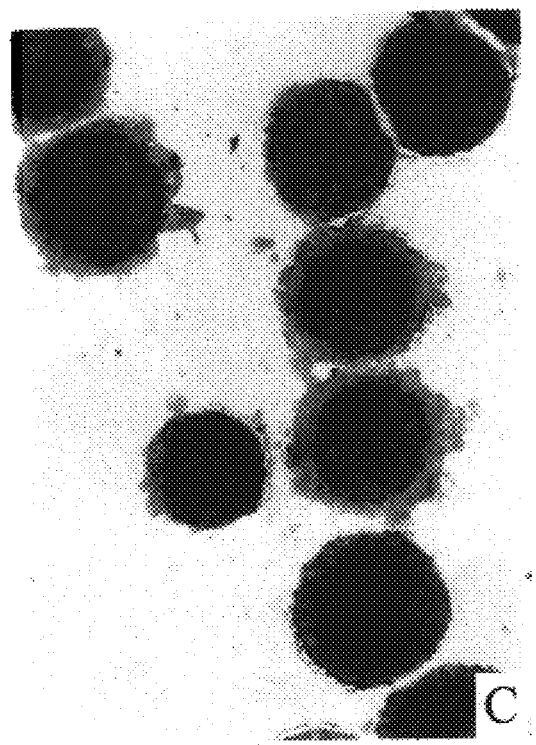
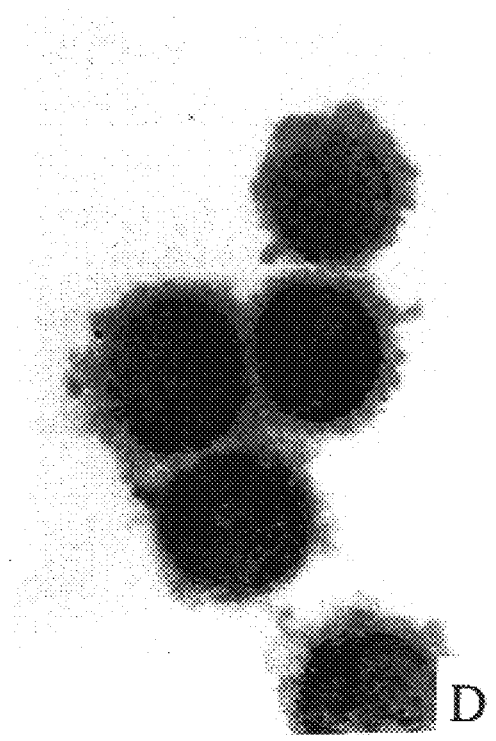

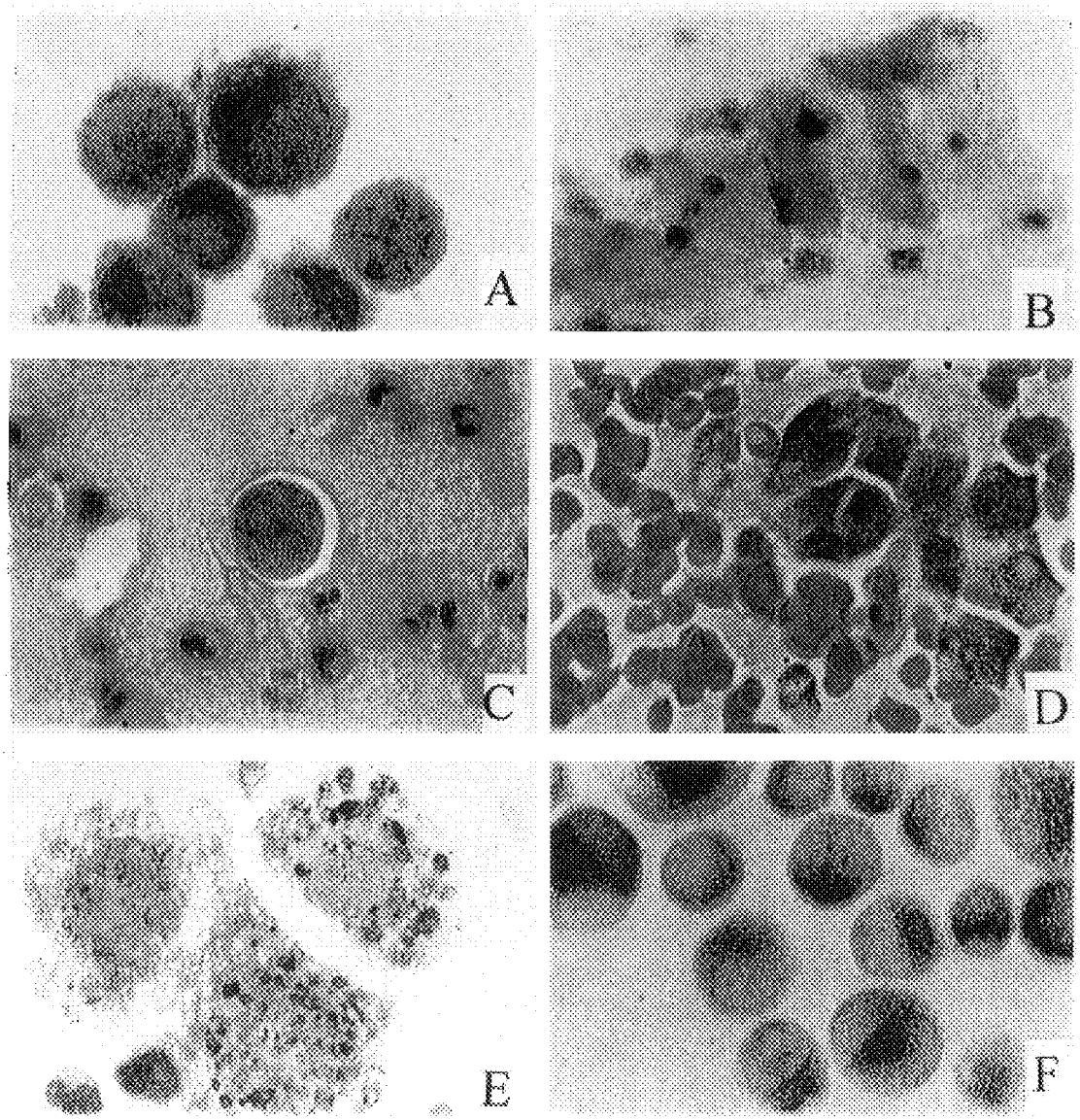
COLOR PLATE 3

CAP-PAP TEST

CROSS-REFERENCE TO OTHER APPLICATIONS

Related Applications

This application continues the Invention Disclosure "CAP-PAP Test for Cervical Cancer Screening," USPTO No. 426850, filed Oct. 24, 1997. (1)

This application claims the benefit of the Provisional Patent Application "(AP-PAP (Cervical Acid Phosphatase-Papanicolaou) Best Processes of Producing and Manner of Using the Same" Ser. No. 60/096,744, filed Aug. 17, 1998. (2)

DEFINITION

The CAP-PAP Test is a new double-staining, single-slide microscopic method that could be developed into an in vitro diagnostic medical device for manual and automatic staining and interpreting of Pap smears for cervical cancer screening, diagnosis of cervical dysplasia and follow-up of therapy. Our idea (novelty) is to use acid phosphatase to label abnormal cervical epithelial cells on Pap smears stained by conventional Papanicolaou technique and, by improving visibility of abnormal cells to improve human perception (sensitivity of automatic instruments) of abnormal cells and interpretation (specificity of automatic instruments) of Pap smears. Increasing accuracy (better sensitivity and at least equivalent specificity with Pap test) the CAP-PAP test could reduce false negative readings of the conventional Pap test—an achievement that could be of benefit to many women.

We are not aware that anybody else has used our technique for the same purpose. The manual version of the test is a rapid, low cost assay, which does not require additional personnel training, and is instantly applicable in all cytopathology laboratories.

The patent protects against infringement of the idea, a process (method, assay) and three products—a diagnostic kit, an automatic processor (stainer) and an automatic evaluation device (digitized image analyzer). Patent protection should cover all rights including manufacture, use and sale.

FIELD OF INVENTION

CAP-PAP Test is an analytical process which involves a chemical reaction to determine presence of a chemical compound (enzyme acid phosphatase) inside cervical cells' cytoplasm (Class 436:A). The test is also an analysis of the chemical properties of the sample (cervical smear) (Class 436: C and E). This is an in vitro testing of a body sample (cell smears or suspension) which may be diagnostic and non-diagnostic of a body condition (Class 128: and 2).

This invention relates to a medical device (process, test, method, assay, diagnostic kit and robotic instrument including automatic stainer and image analyzer), specifically to an improved Pap test for cervical cancer screening, and more specifically to use of an intracellular acid phosphatase chemical reaction product (new marker) for demonstration of cervical cells abnormality. This device is intended for use in prophylactic and diagnostic procedures based on in vitro analysis of tissue samples.

U.S. Patents.

Direct Relation

This application is not directly related to any U.S. patents available in the USPTO and IBM database (3,4).

The USPTO and the IBM Patent Database were queried to reveal if any patent in these two databases could have relation to three phrases combined from the title of our test. The results was as follows.

1. Cervical Acid Phosphatase=0
2. Acid Phosphatase Cervical Cancer=0
3. Acid Phosphatase Papanicolaou=0

Indirect (Remote) Relation

The USPTO Database was searched for the following keywords: cervical, acid phosphatase, Papanicolaou, staining, cervical cells, cervical dysplasia, pap smear, pap test, Pap stain, staining cells, cervical cancer, uterine cancer, smears, vaginal fluid, and cancer enzym* (3). The IBM Patent Server was searched for query "pap smear, cervical acid phosphatase, and acid phosphatase Papanicolaou." (4)

In both databases we found only 27 patents that could have been partially (probably or possibly) related to our invention. They are listed on Table 1 (Appendix)(5). These patents are related to phrases such as acid phosphatase, Pap test, cervical/vaginal cells, cervical/uterine cancer, or methods for their investigations including Papanicolaou staining techniques. However, none of these patents has information on cervical acid phosphatase combined with Papanicolaou staining for cervical cancer screening. The CAP-PAP Test stands alone.

Possibly Related Products from the FDA Database

The FDA Database contains information for medical products approved for interstate trade in the U.S. This database includes a list of medical devices classified according their names, keywords, codes and regulation product numbers. This is the "Classification Names for Medical Devices and In Vitro Diagnostic Products." We have searched this source for the following keywords: test (assay, method, process), cervical, kit, smear, cancer, stain, Papanicolaou, screening, acid phosphatase (6). The following products were found (Table 2)

TABLE 2

RELATED PRODUCTS FROM THE FDA DATABASE

| Product Keywords | Product Code | Class | Product Number |
|---|---|---|---|
| Stain, Papanicolaou | 88JCI | I/E | 864, 1850 |
| Acid phosphatase, cytochemical | 88JCI | I/E | 864, 1850 |
| Cancer, Stain, Papanicolaou | 88HZJ | I/E | 864, 1850 |
| Cervical, kit, smear | 85MCO | III | 0/? |

E = exempt from 510(k) requirement.
? = unknown

All these stains belong to Class I (Devices subject to General Controls), and are exempted from 510(k) requirement. Our application has not been related to any medical device approved for marketing in the U.S.A.

BACKGROUND—PRIOR ART ADVANTAGES AND OBSTACLES

In this section we discuss the conventional Pap test, recent improvements of Pap test, and our preliminary studies that led to discovery and development of the invention.
The Pap test and New Medic al Devices (UDA Approved and Approval Pending) for Improvement of the Pap test.
Pap Test Pap test is the most used and probably the most successful cancer prevention measure currently available (7). It is recommended for prophylaxis of healthy (asymptomatic) women (8).

The staining procedure was introduced by George Papanicolaou almost 50 years ago (9). This procedure dramatically improved detection of cervical cancer in situ and, more important, cervical dysplasia. Both conditions were followed by aggressive treatment including surgery. As a result many lives were saved. The Pap test was born.(10)

Before systematic administration of Pap test, cervical cancer was among the leading causes of death in women with malignant disease. Pap test screening of healthy or oligosymptomatic women resulted in sharp reduction of cervical cancer incidence and mortality rates. Reported are reductions of 80% (Iceland), 70% (U.S.), 50% (Finland) and 34% (Sweden). Recent WHO reports cite that about 4 of every 5 cases of cervical cancer occurs in those countries without screening programs. (11).

The squamocolumnar junction of the uterine cervix is an area of active epithelial cell proliferation creating, particularly in sexually active women, an area of metaplasia (transformation zone). Many factors (i.e., unprotected sexual activity, human papilloma virus [HPV] infection, smoking), may lead to cellular abnormalities, which over a period of time can result in the development of epithelial cell dysplasia or cancer.(12)

Pap test is based on cytological examination of excoriate (abraded), not exfoliative cells. Physicians, using a spatula or a brush scrape mucosal cells from the cervix, at the neck of the uterus, and smear them on a microscopic slide. Smears are sprayed with a fixative and sent to laboratories, where slides are stained by one version of Papanicolaou staining.

Papanicolaou staining procedure has not been patented, or standardized. However, the technique has been studied and advanced from the original recommendation (13). In 1994 Sigma Chem. Co. introduced a kit, Papanicolaou Staining System (Sigma Procedure HT40), attempting to standardize staining. Because the kit was substantially more expensive than individual reagents, many laboratories have not accepted this method. The Pap test remains to be performed in each laboratory according to local preferences.

Technicians read stained smears under a microscope to determine whether a specimen is negative, nonnegative or positive for a body condition. Cytopathologists examine Pap smear under microscope and make cytological diagnosis of body condition (12). There are varying degrees of dysplasia defined by the degree of cellular atypia (Table 2). All types of dysplasia must be observed and treated as precancerosis (conditions that may lead to cancer)(14).

TABLE 3

CLASSIFICATION SYSTEMS FOR PAPANICOLAOU SMEARS

| Numerical | Dysplasia (cytological) | CIN | Bethesda System | CAP Score |
|---|---|---|---|---|
| 1 | Benign | Benign | Normal | <100 |
| 2 | Benign with inflammation | Benign with inflammation | Normal-Benign-Infection-Reactive ASCUS/AGCUS | >100 + inflammatory cells |
| 3 | Mild dysplasia | CIN I | Low grade SIL* | >150 |
| 3 | Moderate dysplasia | CIN II | ASCUS/AGCUS High grade SIL | TBD** TBD |

TABLE 3-continued

CLASSIFICATION SYSTEMS FOR PAPANICOLAOU SMEARS

| Numerical | Dysplasia (cytological) | CIN | Bethesda System | CAP Score |
|---|---|---|---|---|
| 3 | Severe dysplasia | CIN III | | TBD |
| 4 | Carcinoma in situ | | | TBD |
| 5 | Invasive cancer | Invasive cancer | Invasive cancer | >350 |

*SIL = squamous intraepithelial lesion.
**TBD = to be determined.
CAP Score = cervical acid phosphatase activity (our preliminary unpublished results).
ASCUS = atypical squamous cells of undetermined significance; AGCUS = atypical glandular cells of undetermined significance.

Currently, these classifications (1–4) are used together with evidence of human papilloma virus (HPV) infection. Some strains of HPV have been shown to correlate with poor prognosis (development of cervical cancer) in affected women. Cytopathologists consider a Pap smear to be a medical consultation and will recommend further diagnostic procedures, treatment for infection, and comments on factors that prevent adequate evaluation of the specimen.

The Pap test is purely a prophylactic screening procedure. The presumptive diagnosis is made by cytologic screening of anasymptomatic population with no grossly visible cervical changes. All visibly abnormal cervical lesions should be examined (biopsy). Histological examination of cervical tissue obtained by biopsy is the "golden standard" for cervical cytology. This standard is best defined by criteria for cervical intraepithelial neoplasia (CIN), criteria for cervical cancer and the recent Bethesda System classification. (12). The Pap negative women are referred for next screening test after 6 to 12 months. Nonnegative women are kept on observation with a next exam after three months, or are referred (as well as the Pap smear positive) to gynecological interventions colposcopy and biopsy. This practice has produced dramatic reduction of cervical cancer mortality and morbidity in protected populations.

These positive trends encouraged some of leading workers in the field of cancer prevention to believe that cervical cancer is a curable disease, and that we already have tools for its eradication in the beginning of the $21^{st}$ Century. The major obstacle for reaching this ultimate goal of every disease prevention, is the high rate of false negative readings of the Pap test, during the first (primary) screening.

In 1996, an NIH Consensus Conference on Cervical Cancer revealed that 20% of women with a single negative Pap test, developed cervical cancer in the next five years (7). The Conference recommended to increase frequency of screening (annually), to improve sampling (specimen acquisition) techniques, and to improve staining and interpretation (The Bethesda System Classification). These recommendations were widely accepted.(a).

Indeed, many of the current screening protocols call for every women to repeat the Pap test at least once every year for the next five years. It is estimated, if healthy women comply with this schedule, they would have very low probability (0.1%) to develop cervical cancer within this period. However, the vast majority of women do not comply. Another reason for false negatives, is inherent to the Pap test itself Sampling error (omission to bring to the microscopic slides the abnormal cells otherwise present in vaginal fluids or cervical mucosa), and technical error (omission to detect abnormal cells present on smears) are under thorough investigation, and much effort has been given to improve both techniques.(7)

Recent Improvements of the Pap Test

The NIH Consensus Conference's call for Pap test improvement was followed by major development in medical devices industry. Many new patents and instruments have been developed to improve the accuracy of the conventional Pap test. The new technologies are roughly classified into three categories:

Liquid based smear preparation—to remove unwanted elements and drying artifacts. The technology provides excellent smears for image analysis assessment. However, this technology removes debris, but also rare cells that may be diagnostic. (Early detection of cancer is based upon detection of a few malignant cells). Inflammatory cells are removed. This may affect correct diagnosis.

Microscope tracking systems—cytologist's workstation that integrates specimen automated scanning stage. Human participation in decision-making is an integral part of this technology.

Computer-assisted image analysis—to improve detection and interpretation of abnormal cells. Helps human observer during the decision-making processes. Does not replace human assessment.

FDA approved medical devices related to improvement of the Pap test.

Recently, the FDA has approved three technologies, all users of automatic assistance, that claim reduction of false negative readings as their advantage toward the conventional Pap test.

1) ThinPrep Pap Test® (Cytyc, Inc.)

This is a liquid sampling technique. This method is intended to replace the Pap test (only in the Sample preparation phase). After the approval, it has been accepted by the HealthCare Corp. In this technology, a physician collects cervical sample in the usual manner, but rather than smearing a small portion of the cervical cells into a slide, a collection device is rinsed in a vial of preservative solution, capturing virtually all of the cell sample. ThinPrep is instrument that disperses and filters the specimen to reduce blood, mucus and inflammation layer of cells to a microscopic slide. ThinPrep 2000 Processor is offered for diagnosis of cervical cancer, lung, bladder, gastrointestinal cancer, and for fine needle biopsy of thyroid and breast cancer.(15)

Disadvantage of this method is that the final sample does not represent the original sample obtained from a patient. Many "inflammatory" and other cells, removed by this cleaning technology could contribute for diagnosis of the body condition. Many small cancer cells may also be lost during the procedure. Implementation needs additional training of Pap test providers, and cytotechnologists (probably cytopathologists, too), and requires buying new equipment, the ThinPrep 2000 Processor. In borderline cases, other techniques are needed to improve sensitivity (i.e., Digene's Hybrid Capture HPV test). The use of this technology adds about $30.00 to the cost of the conventional Pap test.

2) PapNet® (Neuromedical Systems Inc., NY) (www.nsix.com).

The technology is approved by the FDA for quality control (QC) of the conventional Pap test. All "negative" slides are re-screened by an automated microscope with digital video output. Each cell and cell cluster is analyzed using neural network processing (NNP). NNP is a form of artificial intelligence that has the capacity to "learn," "recognize" and "generalize." Instrument selects 128 cells/clusters for senior cytotechnologist to review "atypical" images. PapNet is particularly good for detection of small atypical cells of high grade lesions that mimic inflammatory cells (16). The cost is $30.00 over the conventional Pap test cost.

Disadvantage of this system is a need for human (high qualified cytologist) interaction after the instrument selected 128 "characteristic" fields. A problem arises during an assessment procedure. This instrument takes images at a single focus and magnification. This is an oversimplification of a microscope as an input device. When a human operator investigates cervical smears using microscopy, he/she always has option to increase magnification and change focus in order to clarify what he/she is seeing and to add more certainty into classification of findings. This is a 3D observation providing more information than any of 2D images or prints that are available to a cytologist interacting with images of microscopic fields already selected by a computer. Computer created images do not have the advantage of human selection.

3) AutoPap® (NeoPath, Inc., WA)(www.neopath.com)

AutoPap was approved by the FDA for quality control screening of "negative" Pap smears. Recently, this system was also approved for the primary screening (new arrivals) of Pap smears.

According to the sponsor, the NeoPath, Inc., the AutoPap Primary Screening System is an automated cervical cytology screening device intended for use in initial screening of Papanicolaou (Pap) smear slides. The device is to be used only on conventionally prepared Pap smear slides and is intended to detect slides with evidence of squamous carcinoma and adenocarcinoma and their usual precursor conditions; it is not intended to be used on slides designated by the laboratory as "high risk." Intended users are trained cytology laboratory personnel operating under the direct supervision of a qualified cytology supervisor or laboratory manager/director. The cost is $20.00 above the cost of the conventional Pap test. (11,11a).

Disadvantage of this method is that it still needs a qualified cytologist to review "negative" slides, and limitation of disease conditions.

4) Accustain® Papanicolaou Staining System (Sigma Chem. Co., St. Louis, Mo.). Procedure HT40 (1994) for research purpose only. (52)

The original Pap test has never been patented. Stains used in the Papanicolaou staining cannot be patented as stains. Instructions for Pap smear staining are vague and permit individual laboratories to adjust dye concentrations and staining time according to requirement of local cytopathologists. Staining characteristics differ from lab to lab and external quality control is difficult to obtain. Accustain is a kit. It was introduced with intention to standardize the Pap staining. We are following the same idea—our kit will be standardized and will provide more staining uniformity than it is currently available. This achievement alone could contribute for reduction of false negative readings.

FDA approval pending medical devices Several systems are still in development.

1) LSC® (Laser Scanning Cytometer, CompuCyte, Corp. MA).

This instrument combines light microscopy, scanning stage, image analysis and multiple staining procedures. This combination was made possible by a strong control of the scanning stage and location of cells. However, staining procedures are subsequent each to other is time consuming, and many artifacts could occur (17).

Human interaction is necessary. (www.compucyte.com).

2) AcCell™ Cytopathology System (AccuMed International, Inc., Chicago, Ill.).

This is a computerized microscope workstation. TracCell™ is a workstation software that integrates specimen automated stage. The system is intended to determine coordinates of areas of "no interest" and to give cytologist only areas "of interest" for observation. Indeed, this approach increases the possibility for misreading of smears (cytologist sees only fraction of the smear).(www.accumed.com)(18)

3) AutoCytePrep and AutoCyteScreen (AutoCyte, Inc. NC).

This one of liquid collection oriented methods, which is advertized as a non-gyn test. Both have improved cell collection and slide/smear preparation yielding to multiple staining (in succession) and more advanced image analysis. An interesting instrument, but needs human interaction for screening.(www.autocyte.com)(19)

4) Hybrid Capture®HPV Test (Digene Corp., MD).

The only approved system for detection of HPV in cervical smears. Reeds women's DNA to identify HPV (infection that may contribute to cervical cancer). It is always perform ed together with the Pap test for morphological determination.(www.digene.com). Can use ThinPrep solution for specimen collection.(20)

5) DiaDexus Joint Venture.

SmithKline Beacham, PLC, and Incyte Pharmaceutical Inc., have recently (December 1998) announced a joint venture "DiaDexus" to study a new test for improvement of the conventional Pap test. Their test uses "antibodies to home in on any abnormal cells in a cervical smear", which could enable them to serve as markers for "replicating cells that are potentially cancerous." Naturally, clinical trials will give the answer. However, it is known that not only cancerous cells replicate, but many other cells, including normal cervical epithelial cells do so. More information is necessary before conclusion on this "new test."(21)

For more information on diagnostics devices available for cervical cancer screening a reader should refer to the recent review articles (22).

Regulatory Issues

All devices described above qualify for category III medical devices, meaning they need to be at least equivalent (safety and efficacy) to an approved device (method) already on the market. However, the "golden standard" to measure safety and efficacy of Pap test related devices is the conventional Pap test itself. And this test has never been standardized or approved as a single in vitro diagnostic device.

A common practice is to use a meta-analysis of data from several cytopathology laboratories using the unstandardized, conventional Pap test, and to create a historic group to be a comparator for the new device. Such a historic group is a very weak comparator for statistical analyses of equivalence. On the other side, all devices described above, have been designed rather as adjunct than a substitute for the conventional Pap test. Therefore, it is very unlikely, they could be able to sustain a scrutiny of statistical analyses in clinical trials (unless with a very large sample size).

We have designed clinical trials to show superiority of CAP-PAP Test versus Pap test to detect cervical dysplasia (and/or cancer). Two of them are competing for SBIR Grants:

BSC-98-02: A Phase I/II Study of the CAP-PAP Test Safety and Efficacy for Cervical cancer Screening in Comparison with the Standard Pap Test. (23).

BSC-98-03: A Phase II Clinical Trial to Compare Safety and Accuracy of the CAP-PAP and the Conventional Pap Test to Detect Precancerosis, and Prevent Cervical cancer in Women with "Nonnegative" Primary Pap Smear. (24)

Our expectation is that our product, a well standardized and controlled kit, will replace the conventional Pap test.

(Please find the SBIR Phase 1 and the SBIR Phase 2 Grant Applications, inclosed in Appendix of this submission).

Summary on Pap test

Clinical trials testing superiority of new technologies vs the conventional Pap test, either have not been completed, or have not demonstrated significant (or trend) superiority. However, they all have shown an increased cost. Recently (April 1999) Medicare reimbursed $7.15 for the Pap test. A proposed legislation tries to limit the lowest reimbursement rate above $14.60 (25). Higher cost per individual test is an inherent problem of all currently available technologies cited above. If implemented, they could significantly (from 10 to 40 dollars a test) increase the cost of primary screening for cervical cancer. With about 80 millions tests per year, it is an extremely expensive task to go. It is not likely the Government (Medicare) or other health insurance companies will proceed using these services. It is more likely, they will continue to search for another, less expensive methods for improvement of th e Pap test, In conclusion, the quest for a reliable, rapid and inexpensive technology that could help eradicate cervical cancer in the next Century, has not been completed yet. We Cervical Acid Phosphatase—Overview of the Prior Art Introduction.

Acid phosphatases are ubiquitary enzymes. They are found in plants and animals. In humans they have been intensely investigated in prostate, liver, kidney and connective tissue, particularly blood cells.(26–29). As enzymes, they all release phosphate from organophosphate. With regard to substrate preference, they have shown species and tissue specificity.

Demonstration of acid phosphatase in tissues and cells is based on enzyme catalysis of organophosphate substrate, caption of phosphate by a metallic ion (i.e. lead), or an organic radical (aromatic ring) by a diazonium salt, formation of a product which is insoluble at acid pH range (pH<5.0), and precipitation of a colorful, granular deposit at sites of enzyme activity (FRP). FRP is available for microscopic examination. The amount is measurable and it is proportional to acid phosphatase activity. (28,30).

Many human cell types and tissues contain acid phosphatase. In humans, acid phosphatase is confined inside lysosome.

Lysosomes are cytoplasmic bodies, 200 to 800 nm in diameter, containing acid phosphatase an d other acid hydrolases. They originate from Golgi membrane or from endoplasmatic reticulum. The enzyme is lipoprotein bound and inactive. Lysosomes play important role in cell defense mechanism Due to abundance of hydrolytic enzymes, lysosomes are involved in both physiologic processes as atrophy and involution, and pathologic processes as cytolysis, necrosis, metaplasia (cytolysosomes). If hydrolytic enzymes are released outside cell, they affect surrounding cells and membranes producing hydrolysis of their structures. It is believed, release of these enzymes from malignant cells substantiate local spread (invasion) of cancer tissue.

Acid phosphatase is abundant in metabolically active cells in inflammation and malignancy.

Medical literature contains many data related to acid phosphatase activity in different human cells and tissues (31–35). Acquired knowledge is helpful as guidance for understanding of the mechanisms involved in the cervical acid phosphatase testing. The alteration of synthesis, processing and trafficking of lysosomal enzymes in malignancy has been demonstrated (36–38). A consistent increase of lysosomal enzymes (i.e., prostatic acid phosphatase) has been found in tumor cells in comparison with their normal counterparts (29,39,40). This property contributes to "aggressiveness" of malignant cells. In blood cells, an increase of acid phosphatase activity was found in connection with infection and inflammation (i.e., PMN, monocytes). Further reference on this matter can be found in review articles (22).

There are many studies in forensic medicine that are all related to demonstration of semen acid phosphatase in vaginal fluid as evidence for sexual intercourse. Information of acid phosphatase activity in cervical epithelial cells is scarcely.

Cervical Acid Phosphatase—Clinical Experience

In healthy women, normal looking cervical epithelial cells contain alkaline phosphatase. Acid phosphatase has been described rarely if it has been described at all. However, acid phosphatase in vaginal fluid/smears has been suited intensely in forensic medicine as indicator of rape (enzyme from semen). (41).

Medical literature contains only few articles related to cervical acid phosphatase. In 1960, Gross and Kinzie found the gradient of acid phosphatase activity in malignant epithelium to be similar to the normal cervical epithelium; however poorly differentiated, malignant cells had a higher degree of activity (42). They used a Gomori's method for visualization of cervical acid phosphatase. In 1961 Berger showed semiquantitative difference between acid phosphatase activity in basal and malignant cells. Mature cervical epithelial cells did not present that type of activity (43).

In 1974, Malvi et al., described acid phosphatase in carcinoma of the cervix uteri (44). Using a staining technique according to Gomori, they found increased enzyme activity in malignant cells as opposing to "normal" activity in basal cells.

Gomori's method. In 1950 Gomori described a lead nitrate method for demonstration of acid phosphatase in tissue sections.(45). The method was based on action of acid phosphatase upon a buffered (pH 5.0) β-glycerophosphate in presence of lead nitrate. Acid phosphatase split glycerophosphate and newly formed lead phosphate (insoluble at pH 5.0, precipitates at sites of enzyme activity. With yellow ammonium sulfide (added later to the reaction), the presence of acid phosphatase is indicated by a black precipitate of lead sulfate. Some authors found this method less specific than believed, and proposed other methods, generally azo dye techniques for demonstration of acid phosphatase. Today, Gomori's method is rarely used in histochemistry.

In 1978, Panazzolo et al. (46) using the same Gomori's method described acid phosphatase-positive granulations in epithelial cells originating from in the vaginal secretion of 44 patients suffering from cervical (17 cases) and uterine cancer (27 cases). They found a highly increased acid phosphatase activity in preinvasive forms, and less activity in invasive cancers. Discussing data they said:

"Acid phosphatase positive intraepithelial structures are exclusively encountered with particular chromatic intensity and localization features on all cells with slight atypia (originating in preinvasive cancer) while they are quite absent in a typical epithelial cells (from invasive cancers). The possibilities and limitations of Gomori's test in oncological screening of female genitals area are reviewed.

It was only discussion (speculation) based on no data. We were not able to find any follow-up to this study.

Our studies confirmed these old data: cervical acid phosphatase can be found only in abnormal cervical epithelial cells.

Preliminary study: Development of the CAP-PAP T est.

In 1986–88, we were investigating a number of human tissue specimens versus many cytochemical techniques to select candidates for quantitative image analysis. In one of series, cervical smears were exposed to cytochemical techniques for demonstration of lysosomal enzymes. Surprisingly, acid phosphatase activity was found in atypical squamous epithelial cells while normal-looking cells did not present this type of activity.(47). We used an azo dye diazonium salt technique. Reviewing literature we found only few articles. The authors, using Gomori's method have come to similar findings. It was obvious that we were the first to demonstrate acid phosphatase activity inside abnormal cervical cells using a diazonium dye staining technique. (1,2,48).

Pursuing this finding, we initiated and designed two studies. Because of various reasons, none of them was completed or published. For the purpose of this patent application we describe here some of crucial findings from those studies.

1987/88 Study: Method for Visualization of Cervical Acid Phosphatase

In 1987/88 we used a double-slide, single-staining technique. It was a small study. Fifty randomly selected women with some kind of pelvic disorders agreed to allow doctors to use their Pap specimen and to smear the spare material onto an additional slide. Two unfixed smears were prepared in doctor's office and sent to laboratory. Within few hours, one of them was stained by Papanicolaou technique (control). The other was stained for acid phosphatase (test). We used a Sigma procedure for staining leukocyte acid phosphatase Cat. No. 387-A and 386-A)

Sigma: Peripheral blood or bone marrow preparations are fixed to a microscope slide. The resulting film is incubated in a solution of naphthol AS-BI phosphoric acid and freshly diazotized fast garnet GBC. The following reaction occur

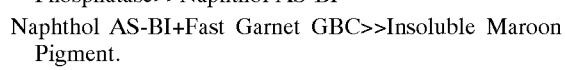

Both smears were independently, but open-label, reviewed by a cytopathologist, a cytochemist and a hematologist. We compared both smears using morphologic criteria for detection of cervical intraepithelial neoplasms (C,N classification). Our conclusions are summarized on the following table.

TABLE XX

Cervical Acid Phosphatase, CIN Classification of Cervical Smears, and Cervical Epithelial Cell Type (Study: CAP-HUP-1986)

| CIN | Dominant cell type >85% of cells | Cell type distribution | Cell characteristics | CAP Result |
|---|---|---|---|---|
| 0 | LCC | L | Large epithelial cell, abundant clear | 0, + |

TABLE XX-continued

Cervical Acid Phosphatase, CIN Classification of Cervical Smears, and Cervical Epithelial Cell Type (Study: CAP-HUP-1986)

| CIN | Dominant cell type >85% of cells | Cell type distribution | Cell characteristics | CAP Result |
|---|---|---|---|---|
| | | | cytoplasm, small nucleus, condensed chromatin | |
| 1 | MCC | L > M > S | Moderate size epithelial cell, abundant cytoplasm, larger nucleus, nucleolus absent, chromatin pattern dense | +, ++ |
| 2 | | M > S > L | | |
| 3 | SCC | S > M > L | Small epithelial cell, C/N = 1.5 and above, large nucleus, nucleoli present | ++, +++ |

CC = cervical cells; L = large, M = intermediate; S = small

This study was not completed and data were not published or presented (48,49). However, this study served as a breadboard for experiments that ultimately resulted in our invention.

1996–97 Study: Conceiving the Idea

In 1996 the NIH Consensus Statement on Cervical Cancer revealed that 20% of women with a single negative single Pap test developed cervical cancer during the following five years. Among other recommendations, the Consensus Conference emphasized needs for technical improvement of the Pap test technology. (7).

We thought we have a new marker which seemed specific for abnormal cervical epithelial cells. Would it be the answer to the problem? To repeat our old findings we designed a small study. Fifteen women, referring to a doctor's office for pelvic exam or regular Pap smear, consented that spare parts of their Pap specimen be used for research purpose. Spare smears were exposed to the CAP procedure (double-slide, single-staining). The results confirmed our observations from 1988: acid phosphatase activity was inversely proportional to maturity of epithelial cells, and abnormal-looking cells possessed most active acid phosphatase.

A double-staining, single-slide method: The CAP-PAP Test.

At this time we have realized that the double-slide, single-staining procedure is not for a routine field application. Therefore we have concentrated our attention to develop a procedure that will provide the benefit of an acid phosphatase marker on the same slide where cells are stained by Papanicolaou staining. The idea was to add a new marker of abnormality to the classical morphologic criteria for cervical cancer screening. To achieve this goal we used HeLa cell line as a breadboard for our experiments. This a human cervical carcinoma derived cell line. All cells contain acid phosphatase activity. We exposed smears of these cells to different cytochemical and Papanicolaou staining conditions. Finally we achieved conditions that could provide simultaneous staining of the marker and cell morphology. The double-staining, single-slide procedure was born. In a follow-up, we applied the new procedure to spare cervical smears. The result confirmed our expectations: acid phosphatase could be stained inside abnormal cervical cells, and counterstained by a modified Papanicolaou (for visualization of classical cytologic criteria). Normal cervical cells did not stain for acid phosphatase. (50, 51). This procedure was named the Cervical Acid Phosphatase-Papanicolaou (CAP-PAP) Test.

The discovery of a new method was followed by an Invention Disclosure (USPTO #426850 of Oct. 24, 1997) (1), and the Provisional Patent Application (USPTO #60/09744 of Aug. 14, 1998)(2).

In 1998, we applied for SBIR grants. The application was under the Fast Track Initiative and included two clinical trials (BSC-98-02 phase I/I, and BSC-98-03, phase II)(23, 24). Due to administrative deficiencies (lack of Business Plan) this application was transferred to a Phase 1 SBIR grant procedure and did not receive funds in this round (Dec. 15, 1998 deadline). We intent to correct deficiencies and to resubmit the application in the first round of 1999.

OBJECTS AND ADVANTAGES

Improvement of the Pap test.

We expect the CAP-PAP Test to add a new parameter (acid phosphatase) for assessment of cervical cells abnormality (structural and functional—biochemical). The Test increases sensitivity of the Pap test cervical cancer screening primary procedures. More women will be classified as "nonnegative," and will be enrolled into further evaluation procedures. This will reduce false negatives (in comparison with the Pap test alone).

The CAP-PAP Test, preserving the Papanicolaou-based morphology for evaluation, keeps the test specificity to be similar to the specificity of the conventional Pap test. Number of false positive will not increase, and there will be no false alarms more than in the conventional Pap test.

There will be no need for additional training of technicians already using the conventional Pap test.

There will be no need for additional equipment in laboratories already using the conventional Pap test.

Multiple slides staining is possible. Except for the period of incubation (60 min, 37° C.), the technician time for performing the CAP-PAP test should be within the range of time necessary for the conventional Pap test (about 30 min). However, the technician is free for other activities during the incubation period.

The CAP-PAP Assay Kit will standardize both CAP and PAP staining procedures and will provide a single reference for all laboratories using the test. Any single reference is now impossible because the Papanicolaou staining procedure has never been patented, there is no standards, and every laboratory uses its own preferential method of staining. Accustain is an exemption, but no many laboratories are using this kit due to its cost. This situation makes difficult comparisons from lab to lab and establishment of national standards. Our CAP-PAP Diagnostic Kit is indented to resolve this problem.

The CAP-PAP staining procedure consists of 24 subsequent steps (alternating staining/washing/drying procedures), and it is easy amenable for automation. A concept for automatic stainer (processor) is included in this patent application.

The cervical acid phosphatase marker enables assessment by an automated image analysis system. The new marker serves as a guide to atypical cells and new software compute cytochemical and morphological parameters to determine degree of cervical dysplasia. Human assessment could provide less information.

A concept for such an instrument is included in this patent application.

Automatic processor (stainer) and a mechanical assess or (image analyzer) provide basis for an integrated expert system (robot) to replace human participation for preparation of stained smears, and for collecting data for evaluation—diagnosis of clinical condition.

A concept for such a system is included in this patent application.

The CAP-PAP Test, as presented in the main embodiment, is user-friendly, rapid, low-cost and reliable method for cancer screening. It may be implemented immediately in all laboratories performing the Pap test. Until the FDA approval (PMA) this test may be used for "research purposes only."

Other Objects and Advantages are:

The CAP-PAP Test is rapid.

Easy for performance.

Easy for assembling all components for successful performance (equipment, reagents, knowledgeable technicians).

Durable (reagents do not change at RT)

Low cost per individual test. The test should not add more than $1.00 above the accepted cost for the Pap test.

Further objects and advantages of our invention will become apparent from a consideration of the enclosed tables, figures and ensuing description.

SUMMARY OF THE INVENTION

This invention relates to an in vitro process (method) which involve:

An in situ chemical reaction for presentation of a chemical compound (more specifically the lysosomal enzyme acid phosphatase) inside cytoplasm of separated abnormal cervical cells (obtained from patients by an approved technique, and smeared on a microscopic slide).

More specifically an intracellular chemical reaction involving acid phosphatase splitting a naphthol substrate and donating the aromatic ring to a diazonium salt—producing an insoluble colorful deposit that precipitates inside cytoplasm at sites of enzyme activity.

A staining procedure (in particular a modified Papanicolaou stain) to visualize morphology of smeared cells, and make smears amenable for microscopic evaluation which may be diagnostic of body condition as well.

A diagnostic procedure utilizing visual characteristics (quantitative and qualitative) of a new marker (cervical acid phosphatase) to detect atypical cervical epithelial cells on Pap smears, a condition which may lead to diagnosis (development) of cervical dysplasia or cancer in asymptomatic women.

More specifically, this invention relates to an in vitro process (method) which utilizes a group of reagents to enter cervical cells smeared on a microscopic slide, induce a specific enzyme reaction, and visualize the presence and activity of the enzyme (acid phosphatase) inside those cells (staining of a marker). This step is followed by another process that utilizes another group of reagents to stain cellular structures and make those cells visible under a microscope (counterstaining, or staining of cell background), and recognizable (classifiable) by morphologic criteria. This part of the process could be manual (preferred embodiment) or automatic (alternative embodiments). The process ends with human (microscopist) or automatic (cell image analysis or related systems) evaluation that utilizes both visual markers (enzyme and cellular morphology) for determination of cervical cells and cervical smear clinical status (detection of abnormality, diagnosis).

The invention also relates to a product (assay, diagnostic kit, medical device), a unique assembly of reagents, instructions (know-how), and control slides, to enable users to perform the CAP-PAP test multiple times evenly and consistently, with or without an automatic device (see 5K.3).

The invention also relates to use of this method (and/or the diagnostic kit with or without an automatic reader [see 5K.3]) for detection of abnormality in cervical cells obtained from cervical mucosa and smeared on microscopic slides. In particular it relates to the use of this technology (process and/or product) for cervical cancer screening purposes.

DETAILED DESCRIPTION

Main Embodiment

Name:

CAP-PAT TEST (Double-Staining Single Slide, Manual Procedure)(CPT1)

Description

Equipment

The Preferred Embodiment is replica of the technicalities involved in staining and evaluation of the conventional Pap test. Our test will not require additional space and/or different equipment, except for a thermostat (for incubation).

Instruments required: Microscope (objective magnification ×10, ×40, and ×100), thermostat at 37° C.

Material required: Small laboratory equipment such as test tubes, appropriate macro and micro pipettes, beakers, Erlenmeyer flasks, staining dishes, stop watch. Speculum, spatula (brush) and microscope slides are needed in the doctor's office. Cover slips will be used in the Lab for permanent mounting of stained smears.

Reagents

Reagents for fixation and marker visualization are available from Sigma Chem. Co.(St. Louis, Mo.)(see Appendix). The following reagents are provided ready for use:

| | | |
|---|---|---|
| R-1 | | Fixative Solution (ex tempore) 25 ml Citrate Solution (Cat No. 95-1) 65 ml acetone, and 8 ml 37% formaldehyde. Place in glass bottle and cap tightly (52). |
| | R-1a. | Citrate Solution Citric acid 18 mmol/L, Sodium citrate 9 mmol/L, Sodium chloride 12 mmol/L, and \ Surfactant, pH = 3.6 + 0.1 (Cat. No. 91-5); |
| | R-1b | Acetone Reagent Grade. |
| | R-1c | Formaldehyde 37% (Catalog N. F. 1637); |
| | R-1d | Sodium Chloride 12 mmol/L |
| R-2 | | Incubation Mixture for acid phosphatase processing. We suggest a modified simultaneous azo dye method according to Burstone and Lojda (53). Reagents for marker visualization are available from Sigma Chem. Co, |
| | R-2a | Naphthyl AS-BI Phosphoric Acid Solution (Cat. No. 387-1), or |
| | R-2a$^r$ | Naphthol AS-BI phosphoric acid 12.5 mg/ml; |
| | R-2b | Fast Garnet GBC Base Solution (Cat. No. 387-2), or |
| | R-2b$^r$ | Fast Garnet GBC base 7.0 mg/ml in 0.4 mol/L hydrochloric acid with stabilizer; |
| | R-2c | Sodium Nitrite Solution (Cat. No. 91-4), or |
| | R-2c$^r$ | Sodium Nitrite 0.1 mol/L; |
| | R-2d | Acetate Solution (Catalog No. 386-3); or |
| | R-2d$^r$ | Acetate buffer 2.5 mol/L, pH = 5.2 + 0.1 |
| R-3 | | Papanicolaou-modified staining of cell morphology. We suggest absolute alcohol instead of denaturated alcohol used in Papanicolaou staining, and Light green instead of Fast green. Duration of some procedures was also changed. Reagents for counterstaining are available from Surgipath Medical Industries, Inc., Richmond, IL: |
| | R-3a | Hematoxylin Solution Gill 3 (Cat. No. 01540); |
| | R-3b | Orange G (OG-6) Solution (Cat. No. 01660), or |
| | R-3b$^r$ | Aqueous stock OG-6 solution 10%, |
| | R-4d | Ethyl alcohol 95%, |

-continued

| | | |
|---|---|---|
| | R-3b[π] | Phosphotungstic acid. |
| | R-3c | Eosin Alcohol (EA-65) Solution (Cat No 01640), or |
| | R-3c[r1] | Light Green in 95% alcohol, |
| | R-3c[r2] | Bismarck brown in 95% alcohol, |
| | R-3c[r3] | Eosin Yellowish and phosphotungstic acid); |
| | R-4d | Ethyl alcohol 95% |
| | R-3d | Ammonium Water (Ex tempore) |
| | R-3d[r] | 0.5 ml Ammonium Hydroxide Solution (Cat. No. ) |
| | R-5b | Distilled water, 100 ml. |
| R-4 to R-6 | Solvents and other reagents are available from different sources. | |
| | R-4a | Ethyl Alcohol concentration 50% |
| | R-4b | Ethyl Alcohol concentration 70% |
| | R-4c | Ethyl Alcohol concentration 80% |
| | R-4d | Ethyl Alcohol concentration 95% |
| | R-5a | Phosphate Buffered Saline |
| | R-5b | Distilled Water |
| | R-5c | Tap Water. |
| R-6 | Glycerol-Gelatin (Cat. No. GG-1) for mounting slides. CAP is a brown-red deposit scattered throughout the cytoplasm of "abnormal" cervical cells. PAP staining produces a color that is combination of original Papanicolaou recommendation: Hematoxylin stains cervical cells nuclei blue, an adds a bluish coloration to the color of cytoplasm. Orange G (OG-6) stains cervical cell cytoplasm orange (red + yellow). Eosin Alcohol (EA-65) stains cervical cell cytoplasm red. However, the Light Green, added to the solution of EA, causes green color of cytoplasm. | |

(Footnote [r]= stock solution)

Storage and stability of reagents:

Store Fixative Solution refrigerated (2°–8° C.). Stability about 2 months. Reagents for marker visualization should also be stored in a refrigerator (2°–8° C.). Discard Naphthol AS-BI Phosphoric Acid Solution if turbidity develops. Citrate Solution should be discarded in the presence of microbial growth. Reagents for counterstaining are kept at room temperature. Reagent labels must bear the expiration date Note: Sigma Catalogue does not contain any reagent or diagnostic kit for visualization of cervical acid phosphatase, or any reference to this enzyme in cervical cells.

Precautions:

All chemicals used in this test are already available on market, they are intended for laboratory use only, and are in compliance with Toxic Substances Control Act (TSCA), PL 9469, Oct. 11, 1976, and Environmental Protection Agency Guidelines (EPA).

Normal precautions exercised in handling laboratory reagents should be followed. Dispose of waste observing all local, state and federal laws.

Fast Garnet GBC Base Solution is toxic. May cause cancer. May cause heritable genetic damage. Cause burns. In case of contact with eyes, rinse immediately with plenty of water and seek medical advice. If you feel unwell, seek medical advice (show the label where possible). Wear suitable protective clothing, gloves and eye/face protection. Keep contained tightly closed in cool well ventilated place (52). Avoid contact and inhalation of Citrate Solution. Target organs: blood and cardiovascular system. Hematoxylin Solution is harmful. Harmful by inhalation, in contact with skin.(For details please see Appendix).

Operation—Manual Operation

Principle of the CAP-PAP Test

We believe the CAP reaction occurs because of the following:

CAP catalyzes the liberation of phosphate from a substrate alpha-naphthyl AS-BI phosphate. The remaining aromatic moiety of the molecule simultaneously couples with Fast Garnet GBC producing an insoluble brown-red diazonium salt on the sites of the enzyme activity. Counterstaining of nuclei is done by Gill 3 hematoxylin and the cytoplasm is counterstained with OG and EA solutions, as described by Papanicolaou (20). CAP activity appears as a distinct red-brown granular deposit on the background of the Pap stained cells (blue nuclei, light blue and/or orange cytoplasm). This allows simultaneous assessment of the CAP activity and the cellular morphology.

However, we do not wish to be bound by this explanation of the staining procedures.

The test includes three phases presented schematically on T ab. 5.

Sample Preparation;

Marker Processing (Fixation, Staining and Counterstaining); and Evaluation (Tab. 5)

TABLE 5

CAP-PAP TEST SCHEMATIC

| Phase; Site | Schematic | Process | Description | Comment |
|---|---|---|---|---|
| 0 Doctor's office | S + Ms = C | Sample preparation | Spatula or brush technique obtained material, and vaginal fluid. Cells smeared on a microscopic slide. Air drying pre-fixation. | Modified Pap test |
| 1 Lab | C + F = CF | Fixation | Citrated acetone-formaldehyde; 30 sec at RT | Modified AP |
| 2 Lab | CF + IM-AP = C[ap] | Staining (Marker) | Incubation Mixture: DW + FG—GBC + Na nitrite + N—AS—BI Incubation: Place slides 60 min, at 37° C. | NOVELTY |
| 3 Lab | C[ap] + Pap = C[ap]$_{PAP}$ | Counterstaining (Morphology) | MODIFICATION: Stain in G3H-rinse; Ammonium water-rinse; Series of alcohol; Stain in OG6-rinse in alcohol>rinse; Mount in glycerol gelatin. | Modified Pap test |
| 4 Lab or Office | C[ap]$_{PAP}$ | Evaluation | CAP + Cervical smear cells morphology in Papanicolaou staining (CIN Classification and/or Bethesda Classification) | NOVELTY (Added criteria) |

S = Sample; Ms = Microscopic slide; C = Cervical cells smeared on microscopic slides; F = Fixative; CF = fixed cells; AP = Staining for cervical cell's acid phosphatase; Pap = Modified Papanicolaou staining; C[ap] = Cervical cells with the acid phosphatase marker; C$_{PAP}$ = cervical cells stained with modified Papanicolaou. C[ap]$_{PAP}$ = Cervical cells stained for acidphosphatase and counterstained with modified Papanicolaou; IM = Incubation mixture.

NOVELTY:
The CAP-PAP Test Processing Formula was defined as:

Patient ➝ Sample Preparation (S + Ms = C) ▸ Marker Processing: Staining © + F = CF + IM = $C^{ap}$) ▸ Counterstaining ($C^{ap}$ + Pap = $C^{ap}_{PAP}$) ➝ Evaluation
(Result: Negative/Nonnegative/Positive).

Procedure—Step by Step
  Sample preparation
  The sample is a group of cervical cells obtained by conventional technique from cervix uteri, and smeared on one or two microscopic slides. Cervical smears are prepared in doctor's office conventionally as for the manual Pap test (except for fixation). A smear for the CAP-PAP test requires no fixation in doctor's office. Smears are air-dried and sent to laboratory for further processing.
  Unfixed smears can be kept at room temperature for several days without appreciable change in CAP activity.
  Marker Processing
  The marker processing procedure includes the following steps: Sample preparation, fixation, maker visualization and counterstaining. Details of this entire procedure are described on Tab. 6

Instructions
  Helpful hints for counterstaining:
  Rinse slides thoroughly after the CAP procedure, as suggested
  Stain in Gill 3 hematoxylin at least 15 minutes.
  Do not overstain with EA. Although still visible, red-brown CAP granules may not be fully remarkable.
  Cytoplasmic counterstaining may be done in one step, by preparing a mixture of equal parts of OG-6 and EA. EA-50 may be used.
  Xylene tends to dissolve partially the FRP obtained in this coupling reaction and should not be used. The use of recommended aqueous mounting medium (glycerol gelatin) does not require dealcoholization in xylene.
Optimized Results
  The "ideal" staining will produce the following results:
  CAP=red-brown individual granules scattered through cytoplasm.
  Other cytological features (nucleus, nuclei, vacuoles, other granulation) easy distinguishable.
  PAP=Transparent colors: nuclei stained violet, cytoplasm stained orange.
Color Plates I–III
  The file of this patent contains at least one photograph executed in color. Copies of theis patent with color photographs are provided by the Patent and Trademark Office with payment of the necessary fee.

TABLE 6

CAP-PAP TEST: STEP BY STEP LABORATORY PROCEDURE

| Phase | Step No. | Container | Procedure | Comment |
|---|---|---|---|---|
| Fixation | 1 | Staining dish | Bring the Fixative Solution to room temperature. Immerse smear in this solution for 20 sec | |
| | 2 | Staining dish | Rinse smear thoroughly in distilled water | Do not allow slide to dry |
| Marker visualization | 3 | Test tube (15 ml) | Combine 0.5 ml Fast Garnet GBC Solution with 0.5 ml Sodium Nitrite Solution. Agitate gently and allow to stand for 2 min at room temperature | Incubation mixture |
| | 4 | Erlenmeyer flask | Transfer the above mixture into the flask containing 45 ml prewarmed distilled water (37 C.) | |
| | 5 | | Add 2 ml Acetate Solution followed by 0.5 ml Naphthyl AS-B Phosphate Solution | |
| | 6 | Staining dish | Transfer the incubation mixture into a staining dish. Immerse smears into this mixture | Incubation |
| | 7 | Thermostat | Cover the staining dish and put it into the thermostat at 37 C. Incubate smear for 60 min protected from light | |
| | 8 | Staining dish | After the incubation rinse smear thoroughly with distilled water | Rinsing |
| | 9 | Staining dish | Dip smear (10 dips) in Phosphate Buffered Saline | |
| | 10 | Staining dish | Rinse in tap water | |
| Counterstaining | 11 | Staining dish | Immerse smear for 15 min in Gill 3 Hematoxylin Solution | (Papanicolaou stain - modified |
| | 12 | Staining dish | Rinse in tap water | |
| | 13 | Staining dish | Treat smear in Ammonium Water (3 dips) | |
| | 14 | Staining dish | Rinse smear in tap water | |
| | 15 | Staining dish | Run smear in 50% alcohol (6 dips) | |
| | 16 | Staining dish | Run smear in 70% alcohol (6 dips) | |
| | 17 | Staining dish | Run smear in 80% alcohol (6 dips) | |
| | 18 | Staining dish | Run smear in 95% alcohol (6 dips) | |
| | 19 | Staining dish | Immerse smear in OG-6 Solution for 3 min | |
| | 20 | Staining dish | Rinse smear with 95% alcohol (6 dips) | |
| | 21 | Staining dish | Repeat step 20 | |
| | 22 | Staining dish | Immerse smear in EA-65 Solution for 3 min | |
| | 23 | Staining dish | Rinse smear in 95% alcohol (6 dips) | |
| | 24 | Staining dish | Repeat step 23 | |
| | 25 | Staining dish | Rinse in distilled water and airdry | |
| Mounting | 26 | Slide | Mount in Glycerol Gelatine | Total Processing Time: 90 min |

Color Plate 1
  Pap smear. CAP-PAP staining. Microscopic magnification .×720
  A. Cytological diagnosis: WNL (within normal limits). A large cervical epithelial cell without any visible activity of cervical acid phosphatase.
  B. Cytological diagnosis: ASCUS+(atypical squamous cells of undetermined origin, probably dysplastic). Two atypical cervical epithelial cells. Left: An intermediate cell with moderate cervical acid phosphatase activity manifested as red-brown granules scattered through cytoplasm. Right: A small abnormal cervical epithelial cell (large, lobulated nucleus, high N/C ratio) with intensive accumulation of CAP marker, identifying higher degree of acid phosphatase activity in this cell.
Color Plate 2
  HeLa cell line specimens. Optimization of the CAP-PAP Test.
  CAP staining produces a red-brown granular precipitate at intracellular sites of enzyme activity. Counterstaining assists presenting cell morphology, cell identification and classification.
  A. CAP+hematoxylin counterstaining. The single-staining, double-slide procedure (CP-2) Acid phosphatase activity abundant. Cellular morphology barely visible.
  B. CAP without counterstaining. Abundant activity of acid phosphatase. Cellular. morphology inadequate.
  C. CAP+conventional Pap. Both acid phosphatase granules and cell morphology recognizable with difficulties.
  D. CAP-PAP. Clear red-brown granular deposit acid phosphatase activity, and cell morphology similar to conventional Pap.
Color Plate 3
  Application of the CAP-PAP test. An example published in the Journal of Histotechnology 1999 (69).
  A. HeLa cell line cells. CAP-PAP staining.
  B. Pap smear. CAP-PAP staining. Cytological diagnosis: within normal limits.
  C. A highly active small dysplastic cervical epithelial cell surrounded by neutrophils.
  Some of neutrophils present acid phosphatase activity (internal control).
  D. Pap smear. CAP-PAP staining. Cytological diagnosis: HSIL. Many intermediate and small dysplastic cervical epithelial cells. All abnormal cells present signs of high acid phosphatase activity. Degree of activity differs among cells.
  E. Pap smear. CAP+hematoxylin. Typical appearance of acid phosphatase positivity: brown-red granules composed of azo-dye precipitate located intracellularly at sites of acid phosphatase activity.
  F. HeLa cell line. CAP+hematoxylin. Typical granular appearance of cervical acid phosphatase activity. Cell morphology barely visible after hematoxylin counter-staining.

USE, Application of the CAP-PAP Test (Manual Procedure)

Application of CAP-PAP Test for Cervical Cancer Screening

The CAP-PAP Test is intended to replace Pap test for primary screening of cervical smears for cervical dysplasia and/or cervical cancer. The test should not be used for exfoliative cytology of vaginal smears.

The following is an insert from our BSC-98-02 Study.(23)

All test group samples ("CAP" smears) will be evaluated as described on Table 7.

TABLE 7

USE OF CAP-PAP FOR CERVICAL CANCER SCREENING

CAP-PAP TEST DECISION MAKING TREE

| Primary Screening CAP criteria | Negative - 1* | Quality Control Re-screening* (n: 1 + 2) | Negative - 3 | |
|---|---|---|---|---|
| | | | Nonnegative - 3 | |
| | Nonnegative - 1* | Diagnosis Pap smear criteria | | Normal/Benign Negative - 4 |
| | Negative - 2 | | Nonnegative - 2 Diagnosis (N-n: 2 + 3) | |
| | | | | Positive (+) ASCUS LSIL HSIL Invasive Carcinoma |

*Pap smear criteria. All slides, or a portion of 10%, or 25% of negative smears.
*Numbers indicate the order when negative or nonnegative slides are diagnosed (selected).

This table shows a two-level decision-making process. At the first level, technicians, performing primary screening, decide whether a smear is cytologically "negative," or it is "nonnegative" and it should be referred to a cytopathologist for a second look."

At this level, the control group will be evaluated according to conventional criteria used for primary evaluation of the Papanicolaou stained smears (Table 8).

TABLE 8

CLASSIFICATION SYSTEMS FOR PAPANICOLAOU SMEARS

| Numerical | Dysplasia (cytological) | CIN | Bethesda System |
|---|---|---|---|
| 1 | Benign | Benign | Normal |
| 2 | Benign with inflammation | Benign with inflammation | Normal ASCUS? |
| 3 | Mild dysplasia | CIN I | Low grade SIL* |

TABLE 8-continued

CLASSIFICATION SYSTEMS FOR PAPANICOLAOU SMEARS

| Numerical | Dysplasia (cytological) | CIN | Bethesda System |
|---|---|---|---|
| 3 | Moderate dysplasia | CIN II | ASCUS? High grade SIL |
| 3 | Severe dysplasia | CIN III | |
| 4 | Carcinoma in situ | | |
| 5 | Invasive cancer | Invasive cancer | Invasive cancer |

*SIL = squamous intraepithelial lesion.
**TBD = to be determined.
ASCUS = atypical squamous cell of uncertain significance.
CIN = cervical intraepithelial neoplasia.
Dysplasia = includes metaplasia and anaplasia.

Currently, these classifications (2–4) are used together with evidence of human papilloma virus (HPV) infection. Some strains of HPV have been shown to correlate with poor prognosis (development of cervical cancer) in affected women. Cytopathologists consider a Pap smear to be a medical consultation and will recommend further diagnostic procedures, treatment for infection, and comments on factors that prevent adequate evaluation of the specimen.

At the first level, the test group will be evaluated according to the CAP-PAP criteria for this level (Table 9)

TABLE 9

NOVELTY CRITERIA FOR PRIMARY SCREENING OF THE CAP-PAP STAINED SMEARS

| CAP Activity | Degree | Visible characteristics | |
|---|---|---|---|
| Per Cell | 0 = Negative | No visible granules | |
| | 1 = Low | Few granules, barely visible | |
| | 2 = Moderate | Several to many granules, clearly visible, scattered through cytoplasm | |
| | 3 = High | Abundance of granules, large granules, aggregates | |
| Per Smear | 0 = Negative | Majority of cells negative; some cells with low activity | |
| | + = Nonnegative | All degrees of positivity: | |
| | | Majority of cervical cells (squamous, parabasal and basal) present some degree of activity (low or moderate). One or two squamous cells, or clusters of cells with high activity. Majority of cells with moderate or high activity. Atypical cell(s) with any degree of activity. | |
| Internal | 0 = Negative | Monocytes - histiocytes | Repeat staining |
| Control of | + = Positive | | Accept results |
| staining | 0 = Negative | Polymorphonuclear neutrophils | Check monocytes |
| procedure on | + = Positive | | Accept results |
| smears | | | |

Decision Level-1

After screening, a technician will have to categorize the smear into one of three options:

YES (Y), meaning there are signs of atypia and this smear may be positive,

No (N), meaning there is no signs of atypia and this smear is negative,

I DON'T KNOW (9), meaning the signs are equivocal suggesting either both Y and N, or neither Y nor N.

Smears bearing decision Y or (s) will be classified as "nonnegative." Only smears for which technicians have been determined as N, will be considered as "negative."

For the purpose of this study only, all "negative" smears from both groups will be re-screened by another technician to minimize the possibility of missing "nonnegative" smears.

Decision Level-2

At the 2d level, all "nonnegative" smears will be evaluated by cytopathologist who will have to diagnose the clinical condition according one of Papanicolaou morphology classifications (Table 3). We prefer the Bethesda System. A cytopathologist evaluating the test group smears will be blinded for results of evaluation of the control group smears, and vice versa.

At the end of evaluation, a cytopathologist will make a categorical decision about the "nonnegative" smear. This decision will have three options:

Negative (technician's assessment was incorrect),

Benign (atypia is present, but there is no sign of malignancy [possible metaplasia]), and Positive (cytological signs of malignancy, either intraepithelial or invasive, are present [possible anaplasia]).

For this study, the final decision at the 2d level, will be either Pap Negative (Pap−, or CP−) (including both "negative" and "benign"), or Positive (Pap+, or CP+) indicating to high risk for cancer development.

Prospective Studies

About the possibility for our test to replace the conventional Pap test, we have designed two clinical trials. One is the *Study of the CAP-PAP Test Efficacy and Safety for Cervical Cancer Screening in Comparison with the Standard Pap Test* (BSC-98-02)(23). This is phase I/II study designed to demonstrate safety of the CAP-PAP procedure, and to compare it with the conventional Pap test according to "surrogate" (laboratory) parameters. In this study we will use the following decision making procedure.

We will compare the incidence of nonnegative smears produced by technicians after reading Pap smears stained by CAP-PAP and Pap test procedure. The primary efficacy endpoint in this study is the "incidence of women whose cervical smears show sign of high risk for cervical cancer and the examining cytopathologist recommended them for biopsy/surgery, or repetition of the Pap test within the next three months." We expect the CAP-PAP will generate about 30% more nonnegative smears. This will reduce the probability for a cytopathologist to miss otherwise Pap(+) smears that might be lost unrecognized in "negative" returns. If this study provide data to support our hypothesis, a further development of the CAP-PAP test will be warranted.

The other clinical trial is *the Acid Phosphatase-Papanicolaou Test Versus Pap West for Prophylaxis of*

*Cervical Cancer.*" (BSC-98-03)(24). This is a phase II study (only because of the size and duration [2.5 years]) to acquire data to test superiority of the CAP-PAP test versus Pap test for early detection of women who will develop clinical outcomes (biopsy [cancer confirmed], surgery or death of cervical cancer) within two years after the Pap test. If this study provide data to confirm superiority of our test, we will design a phase III clinical trial and submit PMA application to FDA, as a prerequisite to marketing a medical device that may be used instead of the Pap test.

Clinical Significance

In cancer prophylaxis, a new test like CAP-PAP should provide at least better sensitivity and similar specificity with the conventional Pap test. We believe a clinical trial will show the CAP-PAP Test is able to select more non-negative women (higher test sensitivity due to acid phosphatase marker) and will reduce the number of false negatives. At the same time, because the criteria for negative/positive are not changed (CIN, Bethesda Classification, based on Papanicolaou staining), we do not expect change of test specificity. The CAP-PAP Test technology does not provide grounds for someone to expect that technicians screening smears, would increase number of false positive readings.

Therefore, the CAP-PAP Test, if implemented in primary screening for cervical cancer, will increase the number of healthy-looking women for further control without the risk of increasing false alarms. For additional information please see Appendix (BSC-98-02, BSC-98-03)

Other Uses:

Cervical Dysplasia

Cervical dysplasia is a term describing changes of normal composition of cervical epithelium. In healthy women, this epithelium is composed of several layer of cells, beginning with basal cells attached to a basal membrane, through intermediate cell layers to the superficial layers of squamous epithelial cells (9,12)

Both scrubbing and brushing excoriation techniques use force to damage cervical mucosal tissue, and to obtain a specimen of this tissue composed of cells from the superficial layers. These cells are smeared on microscopic slide, stained by Papanicolaou technique and evaluated by one of the morphological classifications.

In healthy women this specimen consists of superficial, large squamous cells with relatively small nucleus with condensed chromatin (LCC). Bellow are several layers of intermediate cells (LCC) and, attached to the epithelial basal membrane are the cuboid, small cells with relatively larger nuclei SCC). Local pathological processes (i.e. inflammation, HPV, chronic infections, tumors) could reduce or increase the thickness of mucosal layers, increasing the probability for cells from deeper layers to appear on cervical smears. The most important change could be found when CIN (cervical intraepithelial neoplasia) is present. Depending on the size of the underlying tumor, upper layers are reduced and intermediate and basal cells could be found on cervical smears. This diagnostic condition is called cervical dysplasia. Relation between superficial, intermediate and basal cells present on a cervical smear determines a degree of dysplasia. Sometimes a few cancer cells could be present defining diagnosis of cervical cancer.

Basal cells are biochemically most active and contain more acid phosphatase activity than intermediate, and particularly more than superficial cells which (if typical) are almost without lysosomal activity. Atypical cells usually contain more acid phosphatase activity than "typical cells" at all layers.

All degrees of cervical dysplasia are considered as precancerosis and must be confirmed by clinical procedures (colposcopy, biopsy, surgery) and treated with anti-infective and/or antitumor therapy.(12)

Inflammation

All inflammatory cells contain acid phosphatase. Lysosomal activity is increased during inflammation. However, inflammatory cells (PMN, monocytes) are smaller than cervical epithelial cells, and possess many other morphological characteristics for easy identification by cytotechnologists. Difficulty may appear if basal epithelial cells are involved in an inflammatory process. However, their lysosomal content is significantly smaller than in inflammatory cells of similar size (i.e., monocytes). If necessary, monocyte acid phosphatase can be selectively inhibited to present this difference.

Follow-up of therapy

In equivocal morphology (ASCUS), when cytopathologist cannot decide between Pap(+) and Pap(-) result, he/she usually recommends a repetition of the test within next three months following intensive anti-inflammatory therapy. The CAP-PAP test could provide valuable information of the effect of this therapy on reduction of inflammatory cells, and reparation of cervical epithelium (reduction of acid phosphatase activity).

Quality Control of Pap(-) negative smears.

The acid phosphatase label of cervical cells abnormality may be particularly helpful for the quality assurance during the "rapid review" procedures, when the slides are being reviewed for 30 sec to 1 min. According to Baker and Farrell, rapid review of all negative smears is becoming the most efficient internal quality control measure in cervical cancer screening (54–58)

Ramification

Other Chromogenic Techniques (Papanicolaou-based)

Numerous variants of the original Papanicolaou staining procedure have been published and each laboratory has adjusted the intensity of the nuclear stain, color and depth of the cytoplasmic staining as a matter of personal preference. (13) Users of CAP-PAP test are not discouraged to use their preferred Papanicolaou staining as a counterstaining procedure. Other variants of the standard Pap test when combined with CAP may also prove successful. However, commercial use of this combinations should be prevented by the patent rights covering the CAP-PAP Test, which can be performed with any variant of Papanicolaou staining.

We believe a standard CAP-PAP technology should be used to provide lab-to-lab comparisons and national standardization of the double-staining, single slide test. Toward this goal, we propose a new diagnostic kit for the CAP-PAP Test.

Other Azo-dye Techniques

Intracellular marker visualization is obtained with a simultaneous azo-dye coupling reaction. CAP catalyzes the liberation of phosphate from a substituted naphthyl phosphate inside the cell. The remaining naphthyl moiety simultaneously couples with a diazonium salt (present in the incubation mixture) generating a colored final reaction product (FRP). Different substrate-diazonium salt combinations provide FPP with different color, appearance, substantivity and solubility in acid medium. For the purpose of CAP-PAP test we found alpha-naphthyl AS-BI phosphate/Fast Garnet GBC system the most appropriate regarding all those characteristics. The patent rights should cover all these possibilities because, they all produce a specific colorful granular deposit inside cells, signaling the screener to stop and more thoroughly examine the Pap morphology of the "flagged" cell. The bright color of the CAP deposit, whatever substrate was used, serves as a "cognitive switch" to alert the screener indicating that this cell could deviate from normal cervical cells.

The sharply localized brown-red CAP FRP is also amenable for image analysis assessment (59).

Quality Assurance and Standards

Cervical Carcinoma HeLa Cell Line

Acid phosphatase marker is a granular, colorful deposit inside cytoplasm of cervical epithelial cells. The color (hue, saturation and brightness) and the amount of this deposit depend upon enzyme activity (wanted effect), and upon several technical conditions such as substrate availability (concentration and transmembraneous diffusion), pH, temperature and duration of incubation (cytochemical reaction), solubility and leakage.

In a method development phase we have optimized those technical conditions using the HeLa cell line cells. This cell line is an established (immortalized) human cervical carcinoma cell line (manufactured by ATCC, Fairfax, Va.). We have found (this information is not provided in the cell line description) that HeLa cells contain acid phosphatase (FIG. XX).

---

NOVELTY:

We have modified our method to achieve a uniform distribution of marker in almost all HeLa cells, with an average score of about 300. Under optimal conditions the HeLa cell line cells were >99% CAP positive. Every cell was "flagged" with a red dye deposit (Color Plate 2, FIG. a, f). More than 95% cells were highly positive. The score ranged between 270–290.

---

The technical conditions necessary to produce this type of marker distribution in the HeLa cell line, are recommended for assessment of cervical acid phosphatase activity in cervical cells on our CAP-PAP smears. Therefore, we recommended the HeLa cell line to be used as an external control for our method.

Standard

The uniformity of CAP staining of this cell line permits production of control slides (centrifuged preparation) for the CAP-PAP Test.

In one center (supplier of reagents) the HeLa cell line cells, centrifuged on a microscopic slide and stained by a standardized CAP-PAP procedure. When desired colors will be produced, the entire batch of stained slides will be used for quality assurance as "control slides."

Three slides of this cell line will be necessary for quality control: one stained (positive control) and two unstained to be run with cervical smear staining procedure. At the end, acid phosphatase activity in HeLa cells will be compared with the positive control slide (standard).

Cost-Benefit Estimate

The CAP-PAP test, as presented, is a simple, low cost and rapid assay. It does not require special training for Pap test screeners, or purchasing of additional instruments. Only a microscope is sufficient. Additional cost for reagents per test is less than one dollar. Technical time for marker processing is 3 min plus 60 min incubation time. Duration of counter-staining is about 30 min as for conventional Papanicolaou staining. With 10–20 min for test preparation and post-test cleaning, the entire CAP-PAP procedure should be completed for less than two hours.

Multiple tests can be run simultaneously. If one uses large basket containers for transferring slides between staining dishes, theoretically, an unlimited number of slides can be stained within this time frame.

Our estimate is that CAP-PAP test could be performed for the same price (increased for #1.00) as the Pap test today. (60)

ALTERNATIVE EMBODIMENTS (Description and Operation—Alternative Embodiments. This is a narrative description of the structure and operation of any alternative embodiments of the invention)

CAP-PAP Test-2 (Single-Stain, Double-Slide Procedure). CPT2

Description

The Single-Staining Double-Slide procedure is a composition of cervical acid phosphatase staining on one Pap smear ("CAP" slide) and the conventional Papanicolaou staining on the another Pap smear ("PAP" slide). The procedure is designed for research purpose only. Reagents and instructions are also included in the Diagnostic Kit (vide infra).

Equipment

Same as for the CAP-PAP Test, the Single-Slide, Double-Staining Procedure (CPT1).

Reagents

All reagents (R-1 to R-25) necessary for the CAP-PAP test are needed for the "double" slide CAP-PAP test. Additional reagent is xylene (R-31) for dealcoholization during the conventional Pap procedure, and Permount (R-32) for permanent mount of the Pap slide.

R-31 Xylene (Cat. No. 29,588-4)

R-32 Permount (Cat. No. )

Operation

Principle

The test involves staining of two parallel cervical smears, and this is why the term "double CAP-PAP test" is being used. The first smear is stained with the Papanicolaou staining procedure preferred in the given laboratory. The second, parallel smear serves as a CAP test. The principle of the CAP test is the same as for the CAP-PAP test. Pap stain is without modifications described in the CAP-PAP test Sample preparation Physician obtains cervical sample as for the conventional Pap test. He/she prepares two smears. One, labeled "PAP," for the conventional Pap test is sprayed with one of many commercially available tissue spray-fixatives. Other, labeled "CAP" for acid phosphatase is left to airdry. No fixation is applied in doctor's office to the "CAP" smear. Both smears are sent to a laboratory for further procedure.

Fixation

Fixation of the "CAP" slide is identical to the fixation described previously for the CAP-PAP test.

Marker visualization on the "CAP" slide.

Marker visualization procedure performed on the "CAP" slide is identical to the first phase (step 1–10) of the CAP-PAP test. The counterstaining of the "CAP" slide is done with Hematoxylin Gill 3. Counterstain slide with this solution for 15 min, followed by rinsing in distilled water. This technique is described as step 11–12 of the CAP-PAP Test.

Cell Morphology

The "PAP" slide is stained with the conventional Pap staining procedure. Any variant of the original Papanicolaou staining, optimized in a given laboratory to provide good morphology of cervical cells, is acceptable (13). The Pap test evaluation criteria (CIN and Bethesda Classification) are applied here. (Table 8)

In our preliminary studies we have used a variant of the original Papanicolaou suggested procedure.

The slide marked "PAP" was first immersed in 95% alcohol for 5 min. It was followed by dipping the slide into another fresh 95% alcohol solution 10 times (10 dips). The following 10 dips were done in 80% alcohol.

The next step was staining the "PAP" slide in Hematoxylin Gill 3 for 1 min (Notice the shorter staining in comparison with the CAP-PAP test). Rinse in tap water (10 dips). Immerse in ammonium water (3 dips). Two rinse in two baths of 95% alcohol (10 dips each). The next staining step is in Orange G-6 during 1 min (Note shorter staining with OG-6, then the CAP-PAP procedure).

Two rinse in 95% alcohol (10 dips each). Stain in EA for 7 min (Notice much longer staining time for EA in comparison with the CAP-PAP test). Two rinse with 95% alcohol (10 dips each). Continue dehydration in alcohol with two rinse in 100% alcohol (10 dips each). The last three steps are clearing with xylene 3 baths (10 dips each). Note the differences in the last 3 steps in comparison with the CAP-PAP test. Mounting is also different. The Pap slide is mounted in Permount.

As a result, smears were stained very similar to the conventional Papanicolaou stained cervical smear. Our modification changed this image slightly. Nuclear chromatin was more condensed, and the net structure was less visible (Color Plates. See cell nuclei).

Evaluation

The "CAP" smear is evaluated for presence and degree of acid phosphatase activity among cervical epithelial cells. Well-known cytochemical criteria are used for assessment of enzyme activity. The CAP Score (Table 4) could be used for comparison with other criteria of cervical dysplasia (Table 8). Hematoxylin used to stain the cellular background, allows cytological classification of cells (without Papanicolaou specific criteria related to detection of cancer).

The "PAP" smear is evaluated by the same criteria as in the CAP-PAP Test or the Pap test (CIN or Bethesda classification).

Application—USE

The Double-Slide, Single-Staining procedure is intended for research. It provides opportunity for investigating conditions of the CAP reaction independently of Papanicolaou counterstaining and vice versa. Cross-reference between "CAP" and "PAP" smears (between acid phosphatase activity and cellular morphology) requires a skillful cytopathologist. This parallel staining technique could be of substantial value for further improvement of the CAP-PAP Test.

Because the CAP-PAP Test will be a standardized procedure with internal and external controls, it could be used reciprocally to test the Pap test practices in individual laboratories.

CAP-PAP Test Diagnostic Kit (CPK)

Description

CPK is a ready-to-use body of assembled reagents, instructions, and control slides, to enable users to perform the CAP-PAP test in any cytological laboratory, and by any technician with the common knowledge of the criteria for cervical cancer screening of Pap smears.

Reagents

Same as described in the preferred embodiment plus reagents for the double-slide procedure, (R-1 through R-25)

Instructions (Labeling)

Instructions for use will be included in each box. They will be the same as described for (1) the single-slide double-staining procedure, and for (2) the two-slide double-staining procedure. In addition there will be an explanation how to perform quality control and use control slides or alternative.

Control Slides

Control slides should be used for external control to study the quality of a staining procedures in every laboratory performing the CAP-PAP test. At least four control slides will be provided with each diagnostic kit. Each kit will contain HeLa cells centrifuged on microscopic slides.

The HeLa cell line is derived from human cervical carcinoma (ATCC, CCL-2). Cells are acid phosphatase positive.

One slide will be stained by CAP-PAP test. This is a positive control. Another slide will be stained by Papanicolaou stain only. This is a negative control. Two other smears will be fixed (to stabilize the enzyme until the expiration date), but not stained. They will be used by investigator's laboratory to test their staining procedure.

Packaging

Commercial packaging will be used accordingly to two sizes of the diagnostic kit: 25 and 100 tests per box. Information such as name of the kit, intended use, date of manufacturing, reagents expiration date, name and address of manufacturer, and information about safety, will be clearly displayed according to Federal regulations.

The label "For research purposes only" must be placed on each item before a marketing approval is obtained (after completion of FDA—PMA [pre-marketing approval] application).

A final design of this diagnostic kit will be subject of an additional patent application.

Operation

Principle

The CPK is designed to provide user with standard reagents and controls enabling them for consistent performance and for data comparable with other users and, hopefully, national standards.

HeLa cells are prepared to serve as an external quality control. Two smears will be stained (positive and negative control), and several smears will be fixed but left unstained. They will serve as controls to be run throughout the procedure together with test samples.

Procedure

Use instructions to prepare reagents for staining procedure.

Stain one HeLa cell smear. Compare this slide with the standard control slide.

Adjust your procedure to meet the standard control.

Run the staining procedure with test smears and an unstained control HeLa smear. If desired, a normal blood smear could be used as an additional laboratory control. Observe staining of leukocyte acid phosphatase in polymorphonuclear neutrophils (PMN).

For quality assurance compare the control slide with the standard control smear. If a staining technique is appropriate, more than 99% of HeLa cells, or more than 90% of polymorphonuclear neutrophils should be acid phosphatase positive. If this is the case, accept results. If more than $1/5$ HeLa, or $1/3$ PMN are negative, reject results, and prepare new reagents (solutions). If less than $1/5$ HeLa or $1/3$ PMN are negative, repeat staining with the same reagents.

Evaluate test smears.

Application—USE

CPK will be designed to serve as a tool for replacement of the conventional Pap test for cervical cancer screening. The kit will provide uniform staining, uniform criteria for evaluation, and control slides for intra- and inter-laboratory quality control and assurance. The kit will be low cost, customer-friendly and easy for implementation. It will require no additional equipment and/or technician training.

Cost/Benefit Estimate and Conclusion

CPK is designed to enable users to perform 60 CAP-PAP tests (manually) for about half an hour technician time, plus the incubation (technical) time (60 min). If all reagents are bought separately, ready-to-use, the cost of the entire procedure CAP-PAP would be about $3.00 (CAP=$1.2; PAP=$1.5 per test). Use of CPK with reagents specially prepared for this Kit, should be significantly less expensive than this estimate.

FUTURE DEVELOPMENT

CAP-PAP Assay Processor (CPP)

Description

The CAP-PAP ASSAY PROCESSOR is a multi sample cytological automatic stainer. This instrument is designed to perform the entire CAP-PAP Test (22 steps) in a single run. CPP carries one or more unstained samples (slide/smear) throughout 24 instrument stations where slides are automatically immersed and rinsed in subsequent solutions for appropriate time to produce cervical acid phosphatase marker and cervical cell morphology visible for microscopic evaluation.

Equipment—Main Parts of the Processor

1) Train

Any machine providing step by step (motorized) continuous movement of a chain (with hooks for attaching hangers) or a moving platform in either linear or circular mode.

2) Hanger a rod of specified dimensions which has on one side a hook for attachment to the train, on another side a lever to accept the basket.

3) Basket

Basket-like device to carry on 5–15 slides 4) Station a container with podium (supports glass container), and top (contains stop-watch and crane). Station ON shifts power into Crane. Stop-watch starts when the Crane pick up the Hanger. When Crane returns the Hanger to the Train, stop-watch stops, and the station shuts-off.

Alternative: Podium could be replaced by a moving platform carrying containers containing fixing/staining/washing solutions, Appropriate number of stations can be assembled to provide a series of containers with staining and rinsing solutions in a predetermined order to secure proper CAP-PAP staining.

5) Crane

Any mechanical device providing vertical movement of the attached load under a stop-watch control 6) Thermostat a Chamber Station providing permanent temperature control at 37° C. (dry heat inside the chamber).

7) Fan a Station providing warm/cold fan for drying incoming slides and a storage container.

Reagents

The same reagents as described for the main embodiment (R-1 to R-32)

Operation

Principle

A mechanical device carries-on microscope slides throughout a series of subsequent physico-chemical (fixation/staining/rinsing/drying) steps in order to allow fully automatic processing of acid phosphatase marker and Papanicolaou-modified staining of cell morphology.

Slides for staining are placed into a basket (supports separation of slides and free flow of solutions during staining/rinsing steps). The basket is attached to a train with a hanger. The train has a stepping motor and moves the baskets throughout the procedure (horizontal movement).

When train brings a basket to a station, a timer goes on and activates a crane. The crane receives the basket from the train, and direct it down (vertical movements: up and down) to a staining jar. The timer controls crane movements: DIP (to plunge in liquid and come out quickly), RINSE (wash) and IMMERSE (submerge).

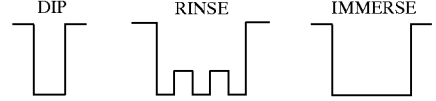

Thermostat provides constant temperature (37° C.) for incubation (immersion of 60 min). Fan dries smears and prepares them for mounting and storage.

Procedure

FIG. 10
CAP-PAP PROCESSOR: STEP BY STEP STAINING PROCEDURE

| Phase | Station No. | Duration; Temperature | Procedure | Comment |
|---|---|---|---|---|
| Fixation | A01 | 20 sec; RT | Immerse slide in the Fixative Solution for 20 sec | |
| | A02 | 15 sec; RT | Rinse slide thoroughly in distilled water. 5 dips | |
| Marker visualization | A03 Preparation of IM— incubation mixture | Test tube (15 ml) | Combine 0.5 ml Fast Garnet GBC Solution with 0.5 ml Sodium Nitrite Solution. Agitate gently and allow to stand for 2 min at room temperature | Incubation mixture |
| | | Erlenmeyer flask | Transfer the above mixture into the flask containing 45 ml prewarmed distilled water (37 C.) Add 2 ml Acetate Solution followed by 0.5 ml Naphthyl AS-BI Phosphate Solution | |
| | | Staining dish | Transfer the mixture into a special dish for incubation. Warm at 37 C. | |
| | A04 Warm | 60 min; 37 C. | Immerse slides in the prewarmed IM. Cover the staining dish and incubate slides at 37 C. for 60 min protected from light | Incubation Thermostat |
| | A05 | 20 sec; RT | Rinse slides thoroughly with distilled water. 5 dips | Rinsing |
| | A06 | 30 sec; RT | Dip slide (10 dips) in Phosphate Buffered Saline | |
| | A07 | 20 sec; RT | Rinse in tap water. 5 dips. | |
| Counterstaining | B01 | 15 min; RT | Immerse slide for 15 min in Gill 3 Hematoxylin Solution | (Papanicolaou stain - modified |
| | B02 | 15 sec. RT | Rinse in tap water. 5 dips | |
| | B03 | 10 sec. RT | Treat slide in Ammonium Water (3 dips) | |
| | B04 | 15 sec. RT | Rinse slide in tap water. 5 dips. | |
| | B05 | 20 sec. RT | Dip slide in 50% alcohol (6 dips) | |
| | B06 | 20 sec. RT | Dip slide in 70% alcohol (6 dips) | |
| | B07 | 20 sec. RT | Dip slide in 80% alcohol (6 dips) | |
| | B08 | 20 sec. RT | Dip slide in 95% alcohol (6 dips) | |
| | B09 | 3 min. RT | Immerse slide in OG-6 Solution for 3 min | |
| | B10 | 20 sec. RT | Rinse slide with 95% alcohol (6 dips) | |
| | B11 | 20 sec. RT | Repeat step 20 | |
| | B12 | 3 min. RT | Immerse slide in EA-65 Solution for 3 min | |
| | B13 | 20 sec. RT | Rinse slide in 95% alcohol (6 dips) | |
| | B14 | 20 sec. RT | Repeat step 23 | |
| | B15 | 15 sec. RT | Rinse in distilled water. 5 dips. | |
| Drying | B16 | 3 min. RT | Airdry: Chamber with fan | |
| Mounting | C01 | 5 min. RT | Mount in Glycerol Gelatine | |

Total processing time: 90 min.
A final design of the CAP-PAP Processor will be subject of an additional patent application.

Application—USE

The stainer is composed of individual stations. This settings provides important flexibility for different staining procedures, not only for the CAP-PAP Test. It also means that the CAP-PAP Test could be automatically performed on many other automatic and semiautomatic slide stainers. We do not envision any of the automatized procedures to be specific for the CAP-PAP test.

CAP-PAP Image Workstation (CPW)

Description

CAP-PAP Digital Tomograph (CPDT) is an image analysis-based software for automatic evaluation of CAP-PAP stained cervical smears. CPDT applies digital image processing methods to the analysis of electronic light microscope images of fixed biological specimens. This software is connected to an image analysis workstation. CPDT connects all parts into a single in vitro diagnostic medical device. This instrument could be optionally used in wide range of different cytochemical and immunocyto(histo)chemical techniques.

Equipment

CAP-PAP Image Analysis Workstation (CPW) is composed of a microscope with a scanning stage (motorized) and automatic focusing (optional), a video camera, a detector, a densitometer (photometric device), a computer (PC in our version) with keyboard and mouse controls, a computer monitor, an image analysis (video) monitor, connecting cables, and an image analysis software CPDT.

In our experiments we have used a customized image analysis system based upon the Imagescan 2 (Carl Zeiss, Thornwood, N.Y.). The main parts of our workstation include, but are not limited to the following.

A) Microscope

A High Resolution Transmitted Light Microscope to produce a real image of microscopic field in focus (specimen of cervical cells smeared on a microscopic slide), and to project it to the system input device. A set of filters was used to transform an incident "white" light (microscope lamp) into a monochromatic (usually green) light to correct for color images and B/W input device.

A Scanning Stage to move the microscopic slide horizontally (x,y axes) under computer control—produce coordinates for location of cells on the slide.

An Auto-focus Device under computer control, to move the stage or an objective lens in vertical dimension (z-axis), to make small correction of focus and to keep sharp images all the time during stage movements.

B) Camera with a Analog to Digital Converter

Usually a TV camera or a scanner are connected to the microscope (ocular end) to convert real images into digital (electronic) signals. They direct electronic signals to a video monitor, a densitometer, and a detector.

C) Image Analysis Video Monitor (see FIG. CP Image Workstation: Video Monitor Display)

This is a TV monitor with a screen capable for simultaneous projection of:

a video image of the microscopic field directed from the TV camera (real time video)

a variable frame directed from the computer, a device that enables selection of images from the microscopic field, and serves as breadboard for projection of the digitized image, a digital image of the selected microscopic field (inside the frame), directed from the computer, a moving cursor (directed from the detector through computer) able to create a dot, a line and/or an area around a feature of interest in the digitized image, a diagram consisting of gray levels versus their number, and two movable thresholds to select digital images according to their optical density, as detected by the densitometer and calculated by the computer.

D) Densitometer

This is a photometric device to measure light intensity coming from the microscopic field. Presence of features like cells, intracellular organelles and other contrast containing structures absorb light an reduce the amount of the light. Light transmitted throughout those features is reduced for the amount of absorption. Negative logarithm of the ratio between transmitted and incident light is a measure of optical density in optics. Densitometer projects to IA monitor two cursors that enable operator to select, by changing grey levels of detection, an area darker than the "white", and lighter than the "black" threshold. This is segmentation of the image according to object density (vertical projection, Z coordinate). Data are directed to the computer for management.

E) Detector-Scanner

This is another photometric device to measure number of electrical signals generated at a certain threshold, above/below a certain threshold, or within a range between a black and a white threshold. Mouse projects a cursor, computer follows cursor movement to project a line or an area on the IA monitor. In case of area measurement, this number of pixels (detected number of signals) could be calibrated into more convenient units of measurement such as micrometers. This is segmentation of the image according to its size (horizontal projection; X & Y coordinates). Data are directed to the computer for management.

F) Variable Frame

This is a modular device to project a measuring window to a video monitor screen and to enable an operator to select features of interest from the projected video image of the microscopic field. Data are directed to a computer for management.

G) Interphase

A mouse, a keyboard, and software designed to combine all instruments with a computer, and put all of them under control of an operator.

H) Computer (Hard and Software)

A simple PC supplied with an image analysis software to put all modules to work together. We have used the Imagescan, a Carl Zeiss built image analysis software (version 2, 1984).

I) Computer Monitor

A standard computer monitor to allow operator numerical data management, preparing and printing results.

K) Printer

Self explanatory.

They were all interfaced as presented on the scheme (See Drawings; FIG. 2)

Operation

Principle of Cell Image Tomography

CIT combines image acquisition and sampling (segmentation), image averaging and background subtraction into a single three dimensional image processing and data management with printout of analytical results.

Plate IV

CAP-PAP Workstation (Version used by the inventors in their preliminary studies)

FIG. 1

The Zeiss Imagescan Workstation assembly: Zeiss Universal microscope, Hitachi CCD camera, IBM PC computer, IBM monochromatic (data) monitor, SONY Trinitron video (color) monitor displaying an actual measuring situation, an operator and the interactive keyboard.

FIG. 2

Video Monitor displaying:

Background: A microscopic view of normal peripheral blood smeared on a microscopic slide (control specimen). Image of the microscopic field is captured by the system camera, and displayed on the TV monitor screen in real time. Many erythrocytes and one polymorphonuclear neutrophil (PMN). Dark color inside PMN cytoplasm is a marker indicating (labeling) esterase activity. [Acid phosphatase produce similar image in HeLa cells and in small dysplastic cervical cells].

Center: a variable frame of 100×100 pixels. A horizontal line (Line: 32) measures the grey levels profile along this line, and serves as indicator for adjustment of thresholds.

Right: a digital image of a cell with marker. This cell was selected (horizontal segmentation) from other cells in the field with a projected multangular closed line (shape of this line is optional—closed circle is needed). Image of the marker is captured between thresholds (X1=40, X2=120) gray levels (vertical segmentation). Computer measures amount of the marker in a tome outlined by vertical and horizontal image segmentation. Data are displayed on Data Management Monitor (FIGS. 1 and 3) in units of area, object light transparency, standard light transparency, optical density and integrated optical density.

Left: measuring diagram (X=gray levels, Y=number of pixels), grey levels profile of the Line 32. Projection of two thresholds. X1=40 gray levels. X2=120 gray levels.

FIG. 3

Data Management Monitor

Upper: Image of an intracellular marker (acid phosphatase) segmented in a tome described by projected circle (horizontal segmentation) and two thresholds, X1=152, and X2=164)

Lower: Image of total cell (dysplastic cervical epithelial) segmented in a tome described by projected circle and two thresholds, X1=60, X2=160).

An installed software instantly calculates relations of marker versus cell, accumulates field information on cell by cell basis, and produces reports of acid phosphatase activity within a population of a certain type of cells.

Manual:

The operator, watching the video screen, selects a cell (or group of cells) of interest and, using the variable frame, selects them from the other portion of the microscopic field image. This creates the X,Y coordinates of the measuring window. Changing thresholds to emphasize density of particular features within the frame, the operator can create Z-coordinates of this window, or to segment a tomus from the entire image. Detector measures area and densitometers measures density of features inside this three dimensional segment.

In a next run, another segment is separated. Computer can easily compute density and area of one vs. another segment, of one or many cells, etc. In case of CAP-PAP related measurement, we measured area and density of acid phosphatase marker, and compared it vs area of cervical epithelial cells containing this contrast, and vs the size of nuclei of these cells.

Automatic:

At preselected size and shape of the variable frame, and thresholds of detection, scanning stage with autofocus, could move the stage automatically. The instrument will accept only selected images and will measure automatically area and density within preselected tomes. Data are compared with a Database information. Instrument makes simple decisions such as "the smear is CAP-PAP test negative/non-negative/positive," printout/display results and narrative explanation. The instrument will not suggest what the patient should do.

Application—USE

Cell Image Tomography Applied for the CAP-PAP Test Related Measurements.

1. Detection of acid phosphatase positive cells on a Pap smear.
2. Measurement of acid phosphatase activity per cell and cell cervical epithelial cell population.
3. Measurement of indexes of dysplasia: relation of acid phosphatase activity vs. cell parameters (size, nucleus etc.).
4. Automatic decision-making. For instance, if acid phosphatase activity cannot be detected, the smear will be classified as negative. If some acid phosphatase activity was present, the machine would be able to determine degree of activity and to compare it with preselected criteria for cervical dysplasia, thus to determine the degree of dysplasia. In that case, smears classified as atypical grade 1 would be reanalyzed, grade 2 would be restrained, and grade 3 would be declared as atypical. This is only an example. Real criteria will be developed in a clinical trial.

A final design of an image analyzer (instrument and software=workstation) will be subject to an additional patent application.

CONCLUSION, RAMIFICATIONS, AND SCOPE

CAP-PAP Test is an analytical process which involves a chemical reaction to determine presence of a chemical compound (enzyme acid phosphatase) inside cervical cells' cytoplasm (Class 436:A). The test is also an analysis of the chemical properties of the sample (cervical smear) (Class 436:C and E). This is an in vitro testing of a body sample (cell smears or suspension) which may be diagnostic and non-diagnostic of a body condition (Class 128: and 2).

CAP-PAP Test intended use is for early detection of cervical dysplasia which may lead to medical intervention/surgery and prophylaxis of cervical cancer. In comparison with the Pap test, the CAP-PAP test increases the sensitivity of cervical cancer screening, and improves the accuracy of the current methodology. This achievement could be accomplished for minimal cost.

a. In the preferred embodiment, the CAP-PAP Test is a double-staining, single-slide microscopic procedure which utilizes intracellular enzyme catalysis of an colorless substrate to produce a colorful deposit (marker) at cytoplasmic sites of enzyme activity, and a modified Papanicolaou procedure to stain cellular structures (morphology) on the same smear. CAP-PAP test is completely different from all new technologies that can increase the Pap test sensitivity, and is something new for the Pap test, too. The CAP-PAP test provides opportunity for instant and simultaneous visual (using microscope and/or image analysis instrument) assessment of cellular morphology and the amount of marker per cell(s). Because the CAP-PAP is based entirely on the original Pap test, the approved standard that is widely used all over the world (standardized techniques, criteria, trained technicians), it does not require additional education of manual technicians and it can be used in every laboratory performing Pap test today. CPK (kit) is intended to standardize not only the CAP-PAP procedure, but the Pap test based cervical cancer screening. This will be additional benefit to many women at risk.

CAP-PAP Test, if applied, could increase the cancer screening cost for $1.00. More than 100 million conventional Pap tests are performed in North America every year. The U.S. alone reports about 80,000,000 Pap tests per year. CAP-PAP is instantly applicable for visual (cytotechnologist, cytopathologist) and automatic (any of newly approved techniques) screening at minimal cost. This is the CAP-PAP test marketing potential.

Ramification

In other embodiments the CAP-PAP Test can be used in automatic staining and evaluation procedures. The CAP-PAP Processor is conceptualized for fully automatic staining. The CAP-PAP Image Analyzer is conceptualized for fully automatic replacement of human participation in the primary screening of cervical cancer. Both instruments may serve as basis for a possible application of robotics technology for cervical cancer screening. This could be the CPT future.

Scope

Our concept to use cervical acid phosphatase is for screening of cervical dysplasia and cervical cancer, is not limited by the procedure described above. Every chemical procedure using a colorless substrate to activate this enzyme to produce a colorful intracellular deposit, can do the same. Also, any chromogen staining technique that may visualize cervical cell morphology after or before cervical acid phosphatase activity is visualized, would produce the same results.

Hereby we extend our request for patent protection of the idea and the process of smear processing and evaluation to all possible methods that can demonstrate cervical acid phosphatase in cervical cells with any variant of Papanicolaou staining. This includes use of all automatic stainers and image analyzing systems, for staining cervical acid phosphatase, and for automatic evaluation of cervical smears based on demonstration of cervical acid phosphatase activity inside abnormal cervical epithelial (squamous) cells.

STATEMENT REGARDING FEDERALLY SPONSORED RESEARCH OR DEVELOPMENT

None

REFERENCE TO MICROFICHE APPENDIX

Not applicable

LITERATURE CITED (Please see the Information Disclosure Statement by Applicant)

1. Invention Disclosure. CAP-PAP Test for Cervical cancer Screening. USPTO #426,850, Oct. 24, 1997.
2. Provisional Patent Application. CAP-PAP (Cervical Acid Phosphatase—Papanicolaou) Test, Processes of Producing and Manner of Using the Same. USPTO #60/096,744, Aug. 17, 1998.
3. USPTO Query. Nov. 12, 1998
4. IBM Query—cervical acid phosphatase, pap smear, acid phosphatase Papanicolaou. Oct. 28, 1998. IBM Query—Individual U.S. Pat. Nos.: 5,257,182; 4,523,278; 4,550,016; 4,206,280; 5,352,613.
5. List of individual patents from the USPTO and IBM databases that could be remotely related to the invention.
6. FDA Query, Oct. 29, 1998
7. NIH Consensus Conference on Cervical Cancer, 1996. NIH, Bethesda, Md. (Http://text.nlm.nih.gov), and Cervical Cancer. NIH Consens Statement Apr. 1–3, 1996; 14(1): 1–38.
8. ACS Screening Recommendations for the Early Detection of Cancer. Web Page: www.texmed.org/health_science/poep/hs_poepcancer.html (Apr. 1, 1999).
9. Papanicolaou GN. A new procedure for staining vaginal smears. *Science* 1948, 95(2469): 438–39.
10. WHO Releases. Report on Cervical Cancer Screening (www.paptest.com/dwnlds/who.txt).
11. Citation from NEOPATH: Clinical Update in Modern Cytology. Automation in Primary Screening. AutoPap. 1998 Neopath. Inc., and Marshall J. AutoPap Experience: False Negative/False positive Problems—Laboratory issues—Clinician Issues—Current Practice vs. AutoPap. Invited lecture. Conference on Automated Solutions in Cervical Cancer Prevention. McLean, Va., Jul. 29, 1998; and NeoPath Inc.: AutoPap Primary Screening System. Web page: www.neopath.com/product (Apr. 1, 1999.
12. Ritchie A C. *Boyd's Textbook of Pathology,* Female Reproductive System, Tumors. Ninth Edition. Lea & Febiger, Philadelphia, 1990; pp. 1365–72.
13. Koss L G. The Papanicolaou Stain. In Koss L G. *Diagnostic Cytology and its Histopathology Basis.* 4$^{th}$ Ed. Lippincott, Philadelphia, 1992; pp. 1474–92.
14. Mac Kay T. H. Cervical intraepithelial neoplasia (CIN: Dysplasia if the cervix). In L. M. Tierney, S. J. McPhee, M. A. Papadakis (Eds) 1997 *Current Medical Diagnosis and Treatment,* 36 ed. Appleton & Lange publishers, 1997; pp. 674–75.
15. Cytus Inc.: The ThinPrep System—How it works. Web Page: www.cytus.com/85506Prd/prepwork.htm. (Apr. 1, 1999).
16. NetMed: Papnet—How Papnet works. Web Page: www.papnet-ohio.com/more.htm (Apr. 1, 1999)
17. CompuCyte, Inc.: The LSC Laser Scanning Cytometer. Web Page: www.CompuCyte.com/prodinfo.html (Apr. 1, 1999).
18. AccuMed Int.: AcCell Cytopathology System. Web Page:www.accumed.com/cyto/accell/html (Apr. 1, 1999).
19. AutoCyte Inc. AutoCyte Prep and AutoCyte Screen for Cervical cancer Screening. Web Page: www.prnewswire.com/cgi-bin/story (story Feb. 9, 1999)( Apr. 1, 1999)
20. Digene: Hybrid Capture Technology. Web Page: www.digene.com/customer/techsup/hcs_tech.htm (Apr. 1, 1999).
21. Diadexus: Diadexsus and Cancer Research Campain Technology. Web Page: diadexus.com/news/releases/980922.html (Apr. 1, 1999).
22. Pizzi A, Metz J L. Diagnostic Cytology Learning Page. Web Site: www-osc.colorado.edu/-metzj/pizzia/learning_page.html (Apr. 1, 1999).
23. BSC-98-02: Study of the CAP-PAP Test Safety and Efficacy for Cervical Cancer Screening in Comparison with the Standard Pap Test. SBIR Phase 1 Grant Application. Dec. 15, 1998 Deadline.
24. BSC-98-03: A Phase II Clinical Trial to Compare Safety and Accuracy of the CAP-PAP and the Conventional Pap Test to Detect Precancerosis, and to Prevent Cervical cancer in Women with "Nonnegative" Primary pap Smear. SBIR Phase 2 Grant Proposal. Dec. 15, 1998, Deadline.
25. NCCC: Worldwide Cervical Cancer Issues. Web Page: www.nccc-online.org/worldcancer.html (Apr. 1, 1999)
26. Goldberg A F, Barka T: Acid phosphatase activity in human blood cells. *Nature* 195:297, 1962.
27. Akimoto S, Mosai M, Akamura K: Tumor marker doubling time in patients with prostate cancer: determination of prostate specific antigen and prostatic acid phosphatase. *Europ Urol* 27:207–12, 1995.
28. Markovic O, Shulman N R: Megakaryocyte maturation indicated by methanol inhibition of an acid phosphatase shared by megakaryocytes and platelets. In *Megakaryocyte Biology and Cellular Properties.* Ewatt B, Levin R (eds), Elsevier North Holland Inc, New York, 1981, pp 271–83.
29. Bunn P: Tumor markers. In *Cecil Textbook of Medicine,* Wingaarden J, Smith L, Bennett C (eds), WB Sounders Co, Philadelphia, 1992, pp 1034–7.
30. Markovic O: Cytochemistry of megakaryocytes. 3. Acid phosphatase. Method for cytochemical investigation. *God Zb Med Fak Skopje* 22: 91–117, 1976. (Three articles)
31. Markovic O, Markovic N: Cytochemistry and immunocytochemistry in the classification of blood marrow and blood cells and in the diagnosis of hematologic disorders. In *Electronmicroscopic Cytochemistry and Immunocytochemistry in Biomedicine.* Ogawa K, Barka T (eds). CRC Press, Boca Raton, 1993, pp. 611–638.
32. Yam LT, Li CL, Lam K W: Tartrate resistant isoenzyme in reticulum cells of leukemic reticuloendotheliosis. *New Engl J Med* 284:357–9, 1971.
33. Van Der Heuvel R, Mathieu E, Schoeters G et al: Stromal cells from murine developing hemopoietic organs: comparison of colony-forming unit of fibroblasts in long-term cultures. *Int J Dev Biol* 35:33–41, 1991.
34. Sidqui M, Collins P, Vitte C et al: Osteoblast adherence and resorption activity of isolated osteoclasts on calcium sulphate hemihydrate. *Biomaterials* 16:1327–9, 1991.
35. Markovic O: Platelet acid phosphatase isoenzymes. II Congress of Yugoslavian Hematologists. *Proceedings* 1:801–5, 1974; and Markovic O: Cytochemistry of megakaryocytes. 2. Acid phosphatase: separation of acid phosphatase isoenzymes. *Mak Med Pregl* 30:19–27, 1975.
36. Scambia G, Benedetti P, Ferradina G et al: Cathepsin D assay in ovarian cancer; correlation with pathologic features and receptors for estrogen, progesterone and epidermal growth factor. *Brit J Cancer* 64:182–4, 1991.

37. Sloane B, Moin K, Sameni M: Membrane association of cathepsin B can be induced by transfection of human breast epithelial cells with c-ha-ras oncogene. *J Cell Sci* 107:373, 1994.
38. Garcia M, Derock D, Pujon P et al: Overexpression of transfected cathepsin D in transformed cells increases their malignant phenotype and metastatic potency. *Oncogene* 5:1809–14, 1990.
39. Saeed S, Stock-Novak D, Pohlod R et al: Prognostic correlation of plasma cell acid phosphatase and beta-glucuronidase in multiple myeloma. *Blood* 78:3281–7, 1991.
40. Zhou R, Sause W T, Hammond E H et al: Correlation of survival with quantitative tissue staining of prostate specific acid phosphatase in patients with prostate cancer. *Int J Radiat Biol Phys* 33: 823–9, 1995.
41. Acid phosphatase in vaginal smears—semen (forensic analyses). List of literature not included in this submission.
42. Gross S J, Kinzie G. Cytochemistry of benign and malignant squamous epithelium of the cervix uteri. Obst and Gynec. 1960;15:261–79.
43. Berger J. Histochemistry of ectopia, ectropion and epidermization. Symposium on premalignant cervical lesions. Acta Cytol. 1961; 5:61–4.
44. Malvi S G, Sirsat S M. A cytochemical study of acid phosphatase in carcinoma of the cervix uteri. The Indian Journal of Cancer 1974; 11(1):81–7.
45. Gomori G. The lead nitrate method for acid phosphatase. In A. G. E. Pierse. Histrochemistry, Theoretical and practical. 3d ed. Williams & Wilkins, 1968, pp. 554, 730.
46. Panazzolo A, Bergantino L, Arrotta S, Napoli F, and Pacilli L. Gli enzimi lisosomiali nella patologia neoplastica del collo dell'utero. Min. Gin. 1978; 30:1123–45. (Italian)
47. Preliminary Studies: Markovic O, Markovic N. Acid phosphatase in cervical cells (unpublished data).
48. Markovic O, Markovic N: May Acid phosphatase decrease Pap test false negative readings. *J Nat Cancer Inst* 89:1459, 1997.
49. Markovic O: Cervical acid phosphatase-Papanicolaou test. *SBIR Project Proposal,* NIH, Bethesda, Md, 1998. (Unpublished Data).
50. Markovic O, Markovic N. Acid Phosphatase in Cervical Smears (CAP-PAP test). Arch Onc 1998; 6(3):137–9.
51. Markovic O, Markovic N, Belledonne M. Cervical Acid Phosphatase-Papanicolaou (CAP-PAP) Test. J. Histotechnology 1999; 22(1):43–47.
52. Sigma Chem. Co. St. Louis, Mo. Sigma technical procedure No 387, 1993; and No.HT40, Papanocolaou Staining System, 1994.
53. Burstone MS: *Enzyme Histochemistry and Its Application in the Study of Neoplasms.* Academic Press, NY, 1962, pp 88–113.
54. Baker A, Melcher D H: Rapid cervical cytology screening. *Cytopathology* 2, 299–301, 1991.
55. Baker R W, WadswortJ, Brugal G et al: An evaluation of "rapid review" as a method of quality control of cervical smears using Axio-Home microscope. *Cytopathology* 8:85–95, 1997.
56. Farrell D J, Bilkhu S, Gibson L, Cummings L et al: Rapid screening of cervical smears as a method of internal quality control. *Acta Cytol* 41:251–60, 1997.
57. Dudding N: Rapid screening of cervical smears: An improved method of quality control. *Cytopatholoay* 6:95–99, 1995.
58. Van Der Graaf Y, Vooijs G P, Gallard H J et al: Screening errors in cervical cytology screening. *Acta Cytol* 31:434–438, 1987.
59. Markovic N, Markovic O, Markovic S: Image processing assisted measurement of intracellular effects of enzyme targeted drugs. *Cell Vision* 2:71–78, 1995.
60. National Coalition for Cervical Cancer. What is the level of reimbursement for the Pap and why is this rate inadequate? Web Page: www.nccc-online.org/ncccfq.asp (Feb. 8, 1999)

We claim:

1. A method for in vitro labeling of abnormal cervical cells with an acid phosphatase enzyme reaction product that increases visibility of said cells on Pap smears, comprising the steps of:
   a) scrapping cervical epithelium by an abrasive device,
   b) obtaining an analytical specimen composed of cervical cells from more than one layer of cervical epithelium,
   c) spreading said specimen over a microscopic slide to form a smear of separated cells,
   d) exposing said smears to air fixation before transporting to a laboratory,
   e) exposing said smears to fixation with a solution containing at least citrate acetone or formaldehyde at room temperature,
   f) incubating said smears, after fixation, with an incubation mixture containing at least a diazonium salt and a naphthol phosphate in water, for time, temperature and pH, optimal for said acid phosphatase reaction to complete,
   g) exposing said smears, after incubation, to staining with a modified Papanicolaou staining method,
   h) mounting said smears after completion of said Papanicolaou staining, and
   i) investigating said smears, after mounting, under a microscope using new criteria for classification of smears stained by the CAP-PAP test,
   whereby said method allow a human observer, or a machine, to diagnose said specimens into categories of negative, nonnegative or positive for cervical dysplasia and/or cervical cancer.

2. A kit which comprises a carrying box comprising:
   a) labeled bottles containing reagents for use in a method for in vitro labeling of abnormal cervical cells with an acid phosphatase enzyme reaction,
   b) control slides, comprising
      (1) microscopic slides with HeLa cells smeared on, and
      (2) microscopic slides stained with HeLa cells, and
   c) written instructions for using said reagents to perform said method on analytical specimens obtained from healthy women or patients, and
   d) written instructions for using said HeLa smears for quality control and/or quality assurance of said method.

3. An assembly of instruments comprising at least
   a) an automatic mechanical device to combine all steps of a method for in vitro labeling of abnormal cervical cells with an acid phosphatase enzyme reaction into a continuous stepwise procedure, comprising:
      i) a train to carry unstained smears throughout a series of stations, and
      ii) a series of stations providing technical facility for performance of every step of the staining procedure, and
      iii) a motor to move said train with smears throughout said stations and said staining procedure,
      whereby said devices are combined into an automatic staining device for processing said marker and making said smears instantly available for human evaluation and classification into categories; and b) an assembly of microscopic image analysis devices comprising at least:
   i) a high resolution microscope,
   ii) an image analyzer, and
   iii) an image recognition software,
   whereby these instruments and software compose an image analysis system, where the microscope produces an image of said smears and projects it into the image analyzer, where the image recognition software automatically compares said image with pre-recorded data necessary for classification of images into negative/nonnegative/positive categories, and produces results of this comparison, and whereby, a composition of said automatic staining device and said image analysis system composes a workstation for performing said method steps from staining to evaluation, automatically and without human participation (robotic).

* * * * *